United States Patent
Wiestner et al.

(10) Patent No.: US 11,384,139 B2
(45) Date of Patent: Jul. 12, 2022

(54) ANTIBODY TARGETING CELL SURFACE DEPOSITED COMPLEMENT PROTEIN C3D AND USE THEREOF

(71) Applicants: The United States of America, as represented by the Secretary, Department of Health and Human Services, Bethesda, MD (US); University of Virginia Patent Foundation, Charlottesville, VA (US)

(72) Inventors: Adrian U. Wiestner, Bethesda, MD (US); Martin W. Skarzynski, North Bethesda, MD (US); Margaret A. Lindorfer, Keswick, VA (US); Ronald P. Taylor, Keswick, VA (US); Christoph Rader, Jupiter, FL (US); Berengere Vire, Les Matelles (FR)

(73) Assignees: The United States of Americans represented by the Secretary, Department of Health and Human Services, Bethesda, MD (US); University of Virginia Patent Foundation, Charlottesville, VA (US)

( * ) Notice: Subject to any disclaimer, the term of this patent is extended or adjusted under 35 U.S.C. 154(b) by 525 days.

(21) Appl. No.: 16/047,929

(22) Filed: Jul. 27, 2018

(65) Prior Publication Data
US 2019/0055305 A1    Feb. 21, 2019

Related U.S. Application Data

(63) Continuation of application No. 15/110,577, filed as application No. PCT/US2015/010620 on Jan. 8, 2015, now Pat. No. 10,035,848.

(60) Provisional application No. 61/924,967, filed on Jan. 8, 2014.

(51) Int. Cl.
| | |
|---|---|
| *A61K 39/00* | (2006.01) |
| *C07K 16/18* | (2006.01) |
| *C07K 16/30* | (2006.01) |
| *C07K 14/47* | (2006.01) |
| *C07K 14/725* | (2006.01) |

(52) U.S. Cl.
CPC ............ *C07K 16/18* (2013.01); *C07K 14/472* (2013.01); *C07K 14/7051* (2013.01); *C07K 16/3061* (2013.01); *A61K 2039/505* (2013.01); *C07B 2200/11* (2013.01); *C07K 2317/24* (2013.01); *C07K 2317/34* (2013.01); *C07K 2317/51* (2013.01); *C07K 2317/515* (2013.01); *C07K 2317/565* (2013.01); *C07K 2317/73* (2013.01); *C07K 2317/732* (2013.01); *C07K 2317/734* (2013.01); *C07K 2317/92* (2013.01); *C07K 2319/03* (2013.01)

(58) Field of Classification Search
CPC .. C07K 16/18; C07K 14/472; C07K 16/3061; C07K 2317/24; C07K 2317/565; C07K 2317/73; A61K 2039/505
See application file for complete search history.

(56) References Cited

U.S. PATENT DOCUMENTS

| | | | |
|---|---|---|---|
| 6,572,856 B1 | 6/2003 | Taylor et al. | |
| 7,923,253 B2 | 4/2011 | Metz et al. | |
| 8,110,369 B2 | 2/2012 | Rump et al. | |
| 8,497,072 B2 | 7/2013 | Hillen et al. | |
| 8,586,006 B2 | 11/2013 | Hood et al. | |
| 10,035,848 B2 * | 7/2018 | Wiestner | C07K 14/472 |
| 2010/0281003 A1 | 11/2010 | Jochim et al. | |
| 2012/0258041 A1 | 10/2012 | Basi et al. | |
| 2013/0029912 A1 | 1/2013 | Holers et al. | |
| 2013/0078245 A1 | 3/2013 | Holers et al. | |
| 2013/0129728 A1 | 5/2013 | Holers et al. | |

FOREIGN PATENT DOCUMENTS

| | | |
|---|---|---|
| JP | 2009-114092 A | 5/2009 |
| WO | WO 90/11779 A1 | 10/1990 |
| WO | WO 97/01578 A1 | 1/1997 |
| WO | WO 97/25351 A2 | 7/1997 |
| WO | WO 2002/101026 A2 | 12/2002 |
| WO | WO 2008/021290 A2 | 2/2008 |
| WO | WO 2009/056631 A2 | 5/2009 |
| WO | WO 2009/074350 A2 | 6/2009 |
| WO | WO 2011/163412 A1 | 12/2011 |
| WO | WO 2012/162565 A2 | 11/2012 |
| WO | WO 2013/143026 A1 | 10/2013 |

OTHER PUBLICATIONS

Brown et al., "Tolerance of single, but not multiple, amino acid replacements in antibody VH CDR 2: a means of minimizing B cell wastage from somatic hypermutation?," *J. Immunol.*, 156(9): 3285-3291 (1996).
Currie et al., "Effect of antigen site and complement receptor status on the rate of cleavage of C3c antigen from red cell bound C3b," *Blood*, 71(3): 786-790 (1988).
Elvington et al., "A targeted complement-dependent strategy to improve the outcome of mAb therapy, and characterization in a murine model of metastatic cancer," *Blood*, 119(25): 6043-6051 (2012).
George et al., "Differential Effects of Anti-β₂-Glycoprotein I Antibodies on Endothelial Cells and on the Manifestations of Experimental Antiphospholipid Syndrome," *Circulation*, 97(9): 900-906 (1998).
Herman et al., "Modeling tumor-host interactions of chronic lymphocytic leukemia in xenografted mice to study tumor biology and evaluate targeted therapy," Leukemia, 27(12): 2311-2321 (2013), Author Manuscript.

(Continued)

*Primary Examiner* — Sheela J. Huff
(74) *Attorney, Agent, or Firm* — Leydig Voit and Mayer, Ltd.

(57) ABSTRACT

An anti-C3d antibody or antibody fragment; method for use thereof to kill cancer cells; and related methods and compositions.

20 Claims, 15 Drawing Sheets

Specification includes a Sequence Listing.

(56) References Cited

OTHER PUBLICATIONS

International Preliminary Report on Patentability, Application No. PCT/US2015/010620, dated Jul. 12, 2016.
International Search Report, Application No. PCT/US2015/010620, dated Apr. 10, 2015.
Kennedy et al., "An anti-C3b(i) mAb enhances complement activation, C3b(i) deposition, and killing of CD20+ cells by rituximab," *Blood,* 101(3): 1071-1079 (2003).
Lindorfer et al., "A novel approach to preventing the hemolysis of paroxysmal nocturnal hemoglobinuria: both complement-mediated cytolysis and C3 deposition are blocked by a monoclonal antibody specific for the alternative pathway of complement," *Blood,* 115(11): 2283-2291 (2010).
Sokoloff et al., "Targeting of cancer cells with monoclonal antibodies specific for C3b(i)," *Cancer Immunol. Immunother.,* 49(10): 551-562 (2000).
Taylor et al., "CD20 mAb-mediated C3b deposition and complement dependent cytoxicity of tumor cells is enhanced by blocking the action of Factor I," *Immunobiology,* 217(11): 1148 (2012), Abstract No. 54.
Tosic et al., "Preparation of monoclonal antibodies to C3b by immunization with C3b(i)-sepharose," *J. Immunol Methods,* 120(2): 241-249 (1989).
Vajdos et al., "Comprehensive functional maps of the antigen-binding site of an anti-ErbB2 antibody obtained with shotgun scanning mutagenesis," *J. Mol Biol,* 320(2): 415-428 (2002).
Written Opinion of the International Searching Authority, Application No. PCT/US2015/010620, dated Apr. 10, 2015.

\* cited by examiner

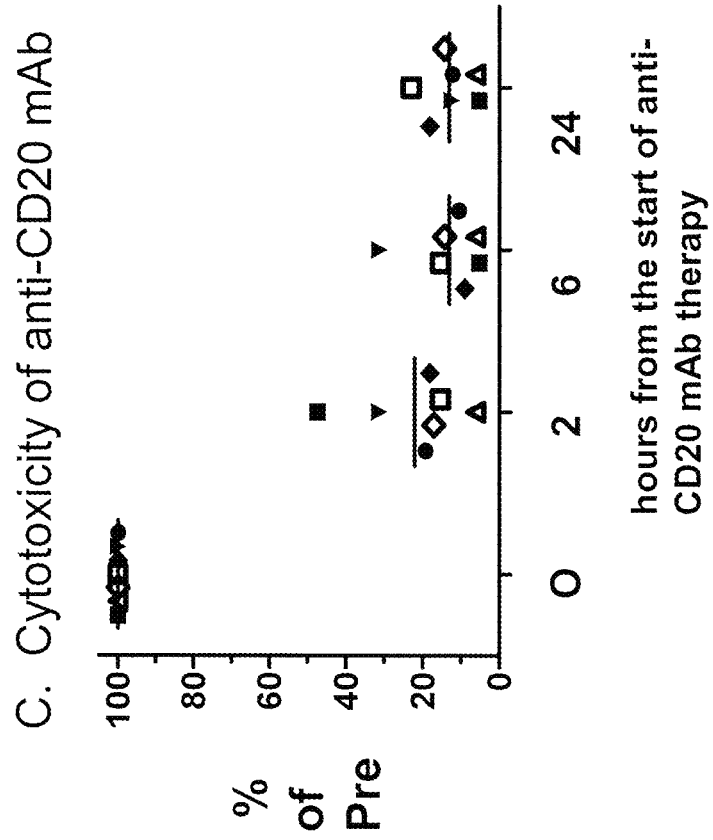

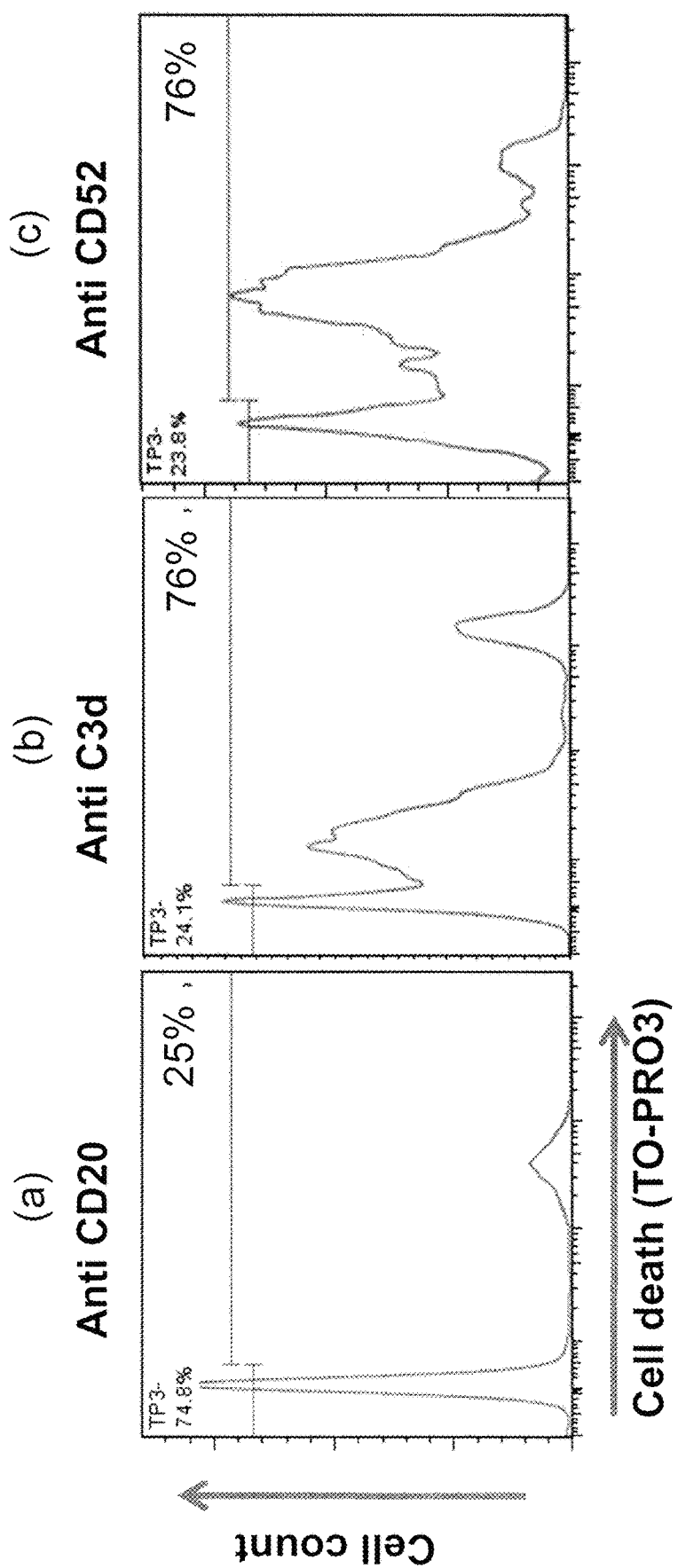

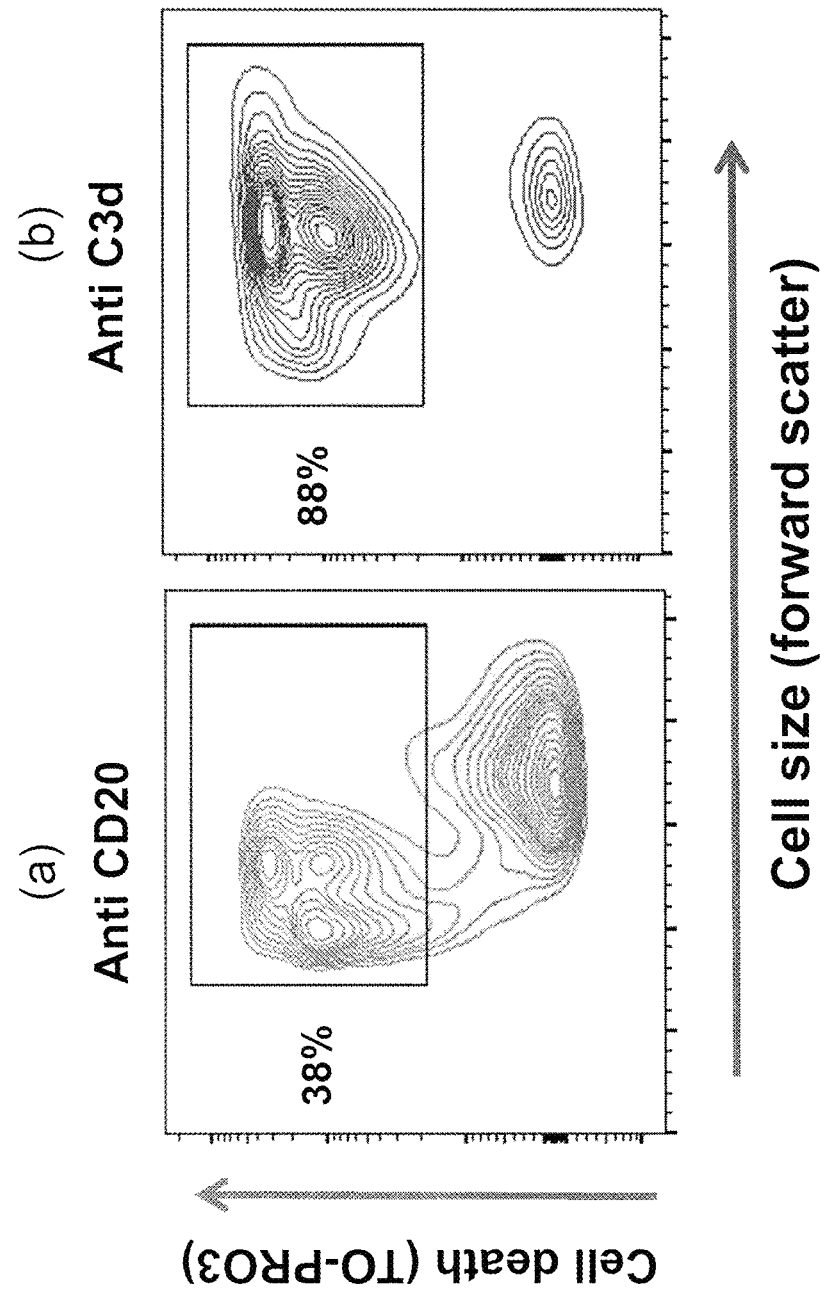

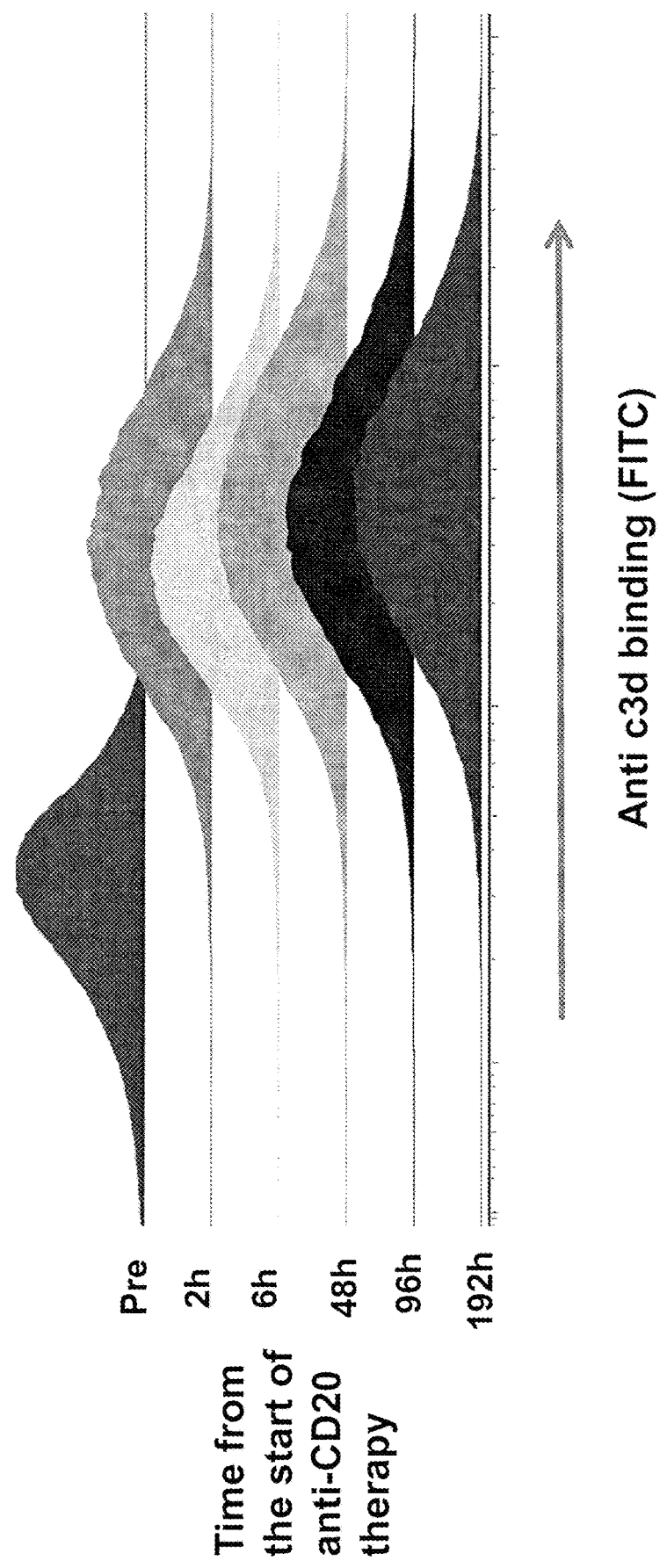

FIG. 7

| Name | Format | Payload | Target | Cancer | Approval |
|---|---|---|---|---|---|
| rituximab (Rituxan®) | chimeric mouse/human IgG1κ | none | CD20 | B-NHL, CLL | 1997, 2010 |
| trastuzumab (Herceptin®) | humanized IgG1κ | none | HER2 | breast | 1998 |
| alemtuzumab (Campath®) | humanized IgG1κ | none | CD52 | CLL | 2001 |
| ibritumomab tiuxetan (Zevalin®) | mouse IgG1κ | 90Y | CD20 | B-NHL | 2002 |
| tositumomab (Bexxar®) | mouse IgG2aλ | 131I | CD20 | B-NHL | 2003 |
| cetuximab (Erbitux®) | chimeric mouse/human IgG1κ | none | EGFR | colon, head and neck | 2004, 2006 |
| bevacizumab (Avastin®) | humanized IgG1κ | none | VEGF | colon, lung, brain, kidney | 2004-2009 |
| panitumumab (Vectibix®) | human IgG2κ | none | EGFR | colon | 2006 |
| ofatumumab (Arzerra®) | human IgG1κ | none | CD20 | CLL | 2009 |
| ipilimumab (Yervoy®) | human IgG1κ | none | CTLA4 | melanoma | 2011 |
| brentuximab vedotin (Adcetris®) | chimeric mouse/human IgG1κ | auristatin | CD30 | HL, ALCL | 2011 |
| pertuzumab (Perjeta®) | humanized IgG1κ | none | HER2 | breast | 2012 |
| ado-trastuzumab emtansine (Kadcyla®) | humanized IgG1κ | maytansine | HER2 | breast | 2013 |
| obinutuzumab (Gazyva®) | humanized IgG1κ | none | CD20 | CLL | 2013 |
| pembrolizumab (Keytruda®) | humanized IgG4κ | none | PD1 | melanoma | 2014 |

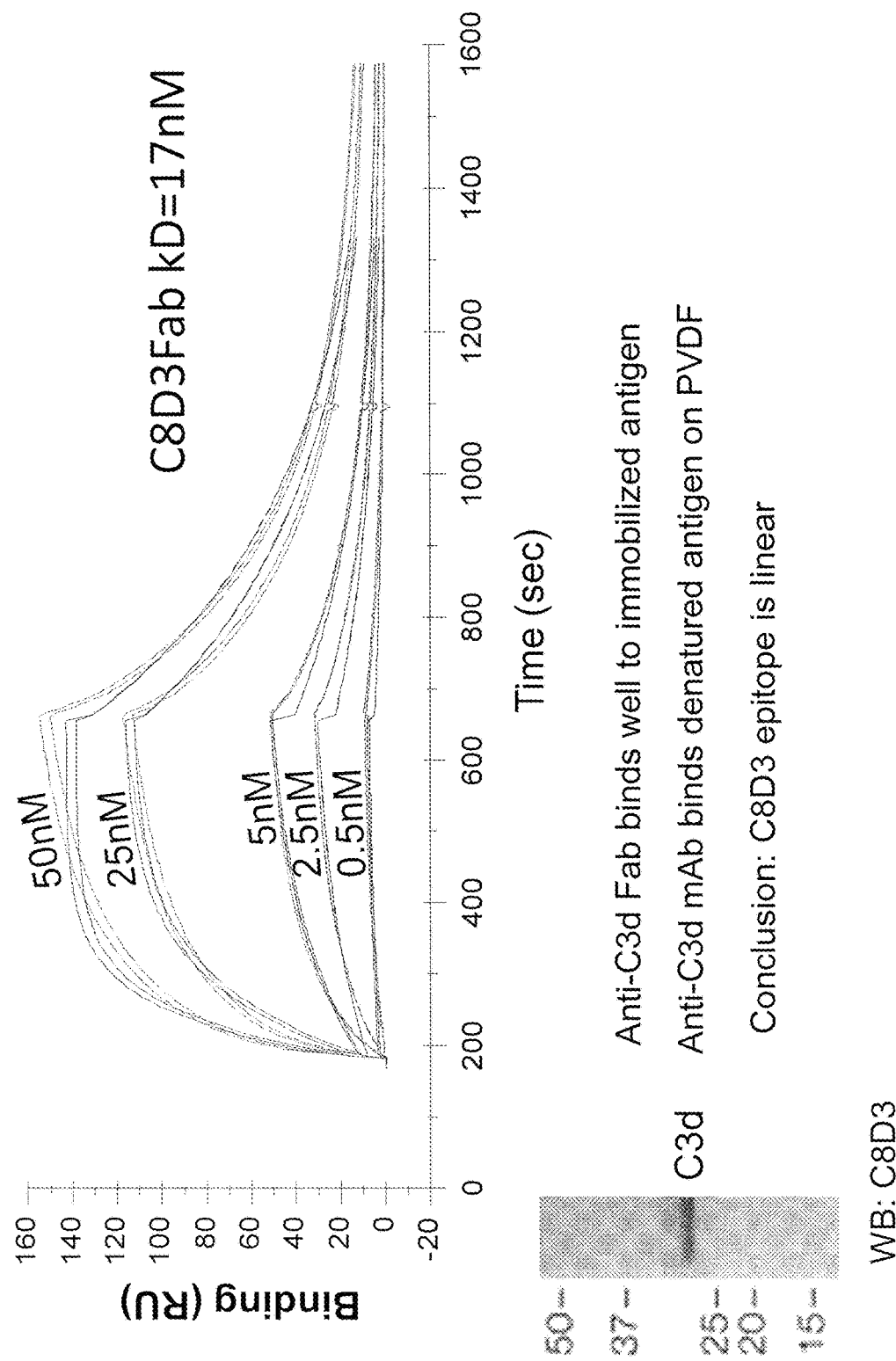

SEQUENCE LISTING

<160> NUMBER OF SEQ ID NOS: 20

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Tyr Pro Gly Asn Gly Asp Thr
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Ala Lys Gly Phe Asp
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Ala Lys Tyr Gly Ser Gly
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Gln Ser Leu Val Tyr Ser Asn Gly Asn Thr Tyr
1               5                   10

<210> SEQ ID NO 6
<211> LENGTH: 3
<212> TYPE: PRT
<213> ORGANISM: Artificial Sequence
<220> FEATURE:
<223> OTHER INFORMATION: Synthetic

```
<400> SEQUENCE: 6

Lys Val Ser
1

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Ser Gln Ser Thr His Val Pro Tyr Thr
1               5

<210> SEQ ID NO 8
<211> LENGTH: 113
<212> TYPE: PRT
<213> ORGANISM: Artificial Sequence
<220> FEATURE:
<223> OTHER INFORMATION: Synthetic

<400> SEQUENCE: 8

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Tyr Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Lys Gly Phe Asp Tyr Trp Gly Gln Gly Thr Thr Val Thr Val Ser
            100                 105                 110

Ser

<210> SEQ ID NO 9
<211> LENGTH: 113
<212> TYPE: PRT
<213> ORGANISM: Artificial Sequence
<220> FEATURE:
<223> OTHER INFORMATION: Synthetic

<400> SEQUENCE: 9

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95
```

Thr His Val Pro Tyr Thr Phe Gly Gly Gly Thr Lys Leu Glu Ile Lys
            100                 105                 110
Arg

<210> SEQ ID NO 10
<211> LENGTH: 114
<212> TYPE: PRT
<213> ORGANISM: Artificial Sequence
<220> FEATURE:
<223> OTHER INFORMATION: Synthetic

<400> SEQUENCE: 10

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Tyr Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Lys Tyr Gly Ser Gly Tyr Trp Gly Gln Gly Thr Thr Val Thr Val
            100                 105                 110

Ser Ser

<210> SEQ ID NO 11
<211> LENGTH: 113
<212> TYPE: PRT
<213> ORGANISM: Artificial Sequence
<220> FEATURE:
<223> OTHER INFORMATION: Synthetic

<400> SEQUENCE: 11

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

Arg

<210> SEQ ID NO 12
<211> LENGTH: 339
<212> TYPE: DNA
<213> ORGANISM: Artificial Sequence
<220> FEATURE:
<223> OTHER INFORMATION: Synthetic

<400> SEQUENCE: 12

```
caggcatatc tgcagcagtc cggggctgaa ctggtgcggc caggggcaag cgtcaaaatg    60
tcatgtaaag caagcggcta ctttcaca tcttactata tgcactgggt gaaacagact     120
ccacgacagg gactggagtg gatcggagca atctaccctg caacggggga caccagctat   180
aatcagaagt tcaaagggaa ggccaccctg acagtggata agagcagcag cactgcttac   240
atgcagctga gttcactgac cagcgaagac tccgccgtct attttgcgc caaggggttt    300
gactactggg gacaggggac taccgtgacc gtctcctca                          339
```

<210> SEQ ID NO 13
<211> LENGTH: 339
<212> TYPE: DNA
<213> ORGANISM: Artificial Sequence
<220> FEATURE:
<223> OTHER INFORMATION: Synthetic

<400> SEQUENCE: 13

```
gatgtggtca tgactcagac ccccctgtcc ctgccagtgt ccctgggcga tcaggcttct    60
atcagttgcc gctcctctca gtccctggtg tacagcaacg gcaataccta cctgcactgg   120
tatctgcaga agcccgggca gtcccctaag ctgctgatct ataaagtgag taaccggttc   180
tcaggagtcc cagaccggtt cagcggatcc ggatctggaa ccgatttcac actgaaaatt   240
agtagggtgg aggccgaaga cctgggcgtc tacttttgtt cacagagcac ccacgtcccc   300
tacaccttcg gcggaggcac taaactggaa atcaagcgt                          339
```

<210> SEQ ID NO 14
<211> LENGTH: 342
<212> TYPE: DNA
<213> ORGANISM: Artificial Sequence
<220> FEATURE:
<223> OTHER INFORMATION: Synthetic

<400> SEQUENCE: 14

```
caggcatatc tgcagcagtc cggggctgaa ctggtgcggc caggggcaag cgtcaaaatg    60
tcatgtaaag caagcggcta ctttcaca tcttactata tgcactgggt gaaacagact     120
ccacgacagg gactggagtg gatcggagca atctaccctg caacggggga caccagctat   180
aatcagaagt tcaaagggaa ggccaccctg acagtggata agagcagcag cactgcttac   240
atgcagctga gttcactgac cagcgaagac tccgccgtct attttgcgc caagtacggt    300
agtggctact ggggacaggg gactaccgtg accgtctcct ca                      342
```

<210> SEQ ID NO 15
<211> LENGTH: 339
<212> TYPE: DNA
<213> ORGANISM: Artificial Sequence
<220> FEATURE:
<223> OTHER INFORMATION: Synthetic

<400> SEQUENCE: 15

```
gatgtggtca tgactcagac ccccctgtcc ctgccagtgt ccctgggcga tcaggcttct    60
atcagttgcc gctcctctca gtccctggtg tacagcaacg gcaataccta cctgcactgg   120
tatctgcaga agcccgggca gtcccctaag ctgctgatct ataaagtgag taaccggttc   180
tcaggagtcc cagaccggtt cagcggatcc ggatctggaa ccgatttcac actgaaaatt   240
agtagggtgg aggccgaaga cctgggcgtc tacttttgtt cacagagcac ccacgtcccc   300
tacaccttcg gcggaggcac taaactggaa atcaagcgt                          339
```

```
<210> SEQ ID NO 16
<211> LENGTH: 17
<212> TYPE: PRT
<213> ORGANISM: Artificial Sequence
<220> FEATURE:
<223> OTHER INFORMATION: Synthetic (C3d Epitope 3)

<400> SEQUENCE: 16

Lys Asp Ala Pro Asp His Gln Glu Leu Asn Leu Asp Val Ser Leu Gln
1               5                   10                  15

Leu

<210> SEQ ID NO 17
<211> LENGTH: 20
<212> TYPE: PRT
<213> ORGANISM: Artificial Sequence
<220> FEATURE:
<223> OTHER INFORMATION: Synthetic (C3d Epitope 1)

<400> SEQUENCE: 17

Pro Asp Gly Val Phe Gln Glu Asp Ala Pro Val Ile His Gln Glu Met
1               5                   10                  15

Ile Gly Gly Leu
            20

<210> SEQ ID NO 18
<211> LENGTH: 33
<212> TYPE: PRT
<213> ORGANISM: Artificial Sequence
<220> FEATURE:
<223> OTHER INFORMATION: Synthetic (C3d Epitope 2)

<400> SEQUENCE: 18

Lys Asp Ile Cys Glu Glu Gln Val Asn Ser Leu Pro Asn Ser Leu Pro
1               5                   10                  15

Gly Ser Ile Thr Lys Ala Gly Asp Phe Leu Glu Asp Phe Leu Glu Ala
            20                  25                  30

Asn

<210> SEQ ID NO 19
<211> LENGTH: 23
<212> TYPE: PRT
<213> ORGANISM: Artificial Sequence
<220> FEATURE:
<223> OTHER INFORMATION: Synthetic (Blocking Peptide)

<400> SEQUENCE: 19

Gln Tyr Gln Lys Asp Ala Pro Asp His Gln Glu Leu Asn Leu Asp Val
1               5                   10                  15

Ser Leu Gln Leu Pro Ser Arg
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic (Scrambled Peptide)
```

```
<400> SEQUENCE: 20

Leu Gln Pro Gln Asn Asp Val Arg Asp His Ser Pro Tyr Glu Leu Gln
1               5                   10                  15

Ser Leu Ala Asp Leu Lys Gln
            20
```

ANTIBODY TARGETING CELL SURFACE DEPOSITED COMPLEMENT PROTEIN C3D AND USE THEREOF

CROSS-REFERENCE TO RELATED APPLICATIONS

This patent application is a continuation of copending U.S. patent application Ser. No. 15/110,577, filed Jan. 8, 2015, which claims the benefit of U.S. Provisional Patent Application No. 61/924,967, filed Jan. 8, 2014, both of which are hereby incorporated by reference in their entireties.

STATEMENT REGARDING FEDERALLY SPONSORED RESEARCH OR DEVELOPMENT

This invention was made with Government support under project number 1ZIHL006070-03 by the National Institutes of Health, National Heart, Lung, and Blood Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 9,956 byte ASCII (Text) file named "739729_ST25.txt" created on Jul. 27, 2018.

BACKGROUND OF THE INVENTION

Monoclonal antibodies (mAbs) have become a mainstay of therapy for many cancers. The key effector mechanisms of mAbs are induction of cell death through complement dependent cytotoxicity (CDC), antibody-dependent cellular cytotoxicity (ADCC), antibody dependent cell-mediated phagocytosis (ADCMP) and in some cases may include induction of apoptosis. The most commonly used mAbs are of mouse origin that have been chimerized or humanized to carry human constant regions (typically the human IgG1 isotype), a requirement for the recruitment of human effector mechanisms.

However, antibody therapy is not completely effective in some applications due to loss of the target surface antigen. For instance, rituximab and ofatumumab are anti-CD20 mAbs that mediate human immune effector mechanisms including CDC as well as ADCC and ADCMP and are approved for patients with Chronic Lymphocytic Leukemia (CLL), a B cell malignancy. Upon infusion of either of these antibodies, complement protein is deposited on the cell surface of CLL cells and a subset of the cells is killed; however, other CLL cells escape, having lost CD20 expression due to a process called trogocytosis by which antibody-CD20 complexes are pulled off the CLL cell surface by immune cells that bind the Fc-portion of the mAb. The process of trogocytosis leading to antigen loss is not limited to anti-CD20 antibodies or lymphoma but appears to be a common event in mAb therapy.

Accordingly, there is a need for new antibody therapies that can overcome problems associated with loss of the targeted antigen.

BRIEF SUMMARY OF THE INVENTION

Provided is an antibody or antibody fragment immunospecific for complement protein C3d. According to one aspect of the invention, the anti-C3d antibody or antibody fragment comprises a heavy chain variable region comprising SEQ ID NO: 3 or 4, or an amino acid sequence with at least 50% sequence identity thereto, as heavy chain complementary determining region-3 (CDRH3). According to another aspect of the invention, the anti-C3d antibody or antibody fragment competes with an antibody comprising a heavy chain variable region comprising SEQ ID NO: 8 and a light chain variable region comprising SEQ ID NO: 9 for binding to C3d, or competes with an antibody comprising a heavy chain variable region comprising SEQ ID NO: 10 and a light chain variable region comprising SEQ ID NO: 11 for binding to C3d.

The invention also provides a method of using the antibody or antibody fragment to kill cells having C3d deposited on their surface.

Further provided is a polypeptide comprising SEQ ID NO: 16, SEQ ID NO: 17, SEQ ID NO: 18; a fragment of five or more contiguous amino acids of SEQ ID NO: 16, 17, or 18; or a combination thereof; wherein the polypeptide has fewer than 50 total amino acids.

Related compositions and methods also are provided as is apparent from the following detailed description of the invention.

BRIEF DESCRIPTION OF THE SEVERAL VIEWS OF THE DRAWING(S)

FIG. 1C is a graph of complement dependent cytotoxicity (CDC) expressed as a percentage of the CDC of cells pre-treatment (% of Pre) plotted against the number of hours post-start of anti-CD20 treatment, demonstrating the resistance to anti CD20 mAb mediated CDC gained by CLL cells within hours upon in vivo treatment with the anti CD20 mAb.

FIG. 2 is a graph showing in vitro binding of different antiC3 mAbs to CLL cells opsonized by complement in vivo as measured by fluorescence intensity (MESF, molecules of equivalent soluble fluorophore). Different mAbs were reacted in the presence of either bovine or human serum (human serum contains C3 protein). mAbs against human complement protein C3 ($\alpha$C3) bind C3d on the surface of cells in the absence of human serum but not in the presence of human serum. Binding of mAbs against human C3d ($\alpha$C3d) to C3d on the surface of cells is not antagonized by human serum components. mAbs against the short-lived human complement protein C3b ($\alpha$C3b) only weakly bind to cells opsonized by complement.

Figure 3:
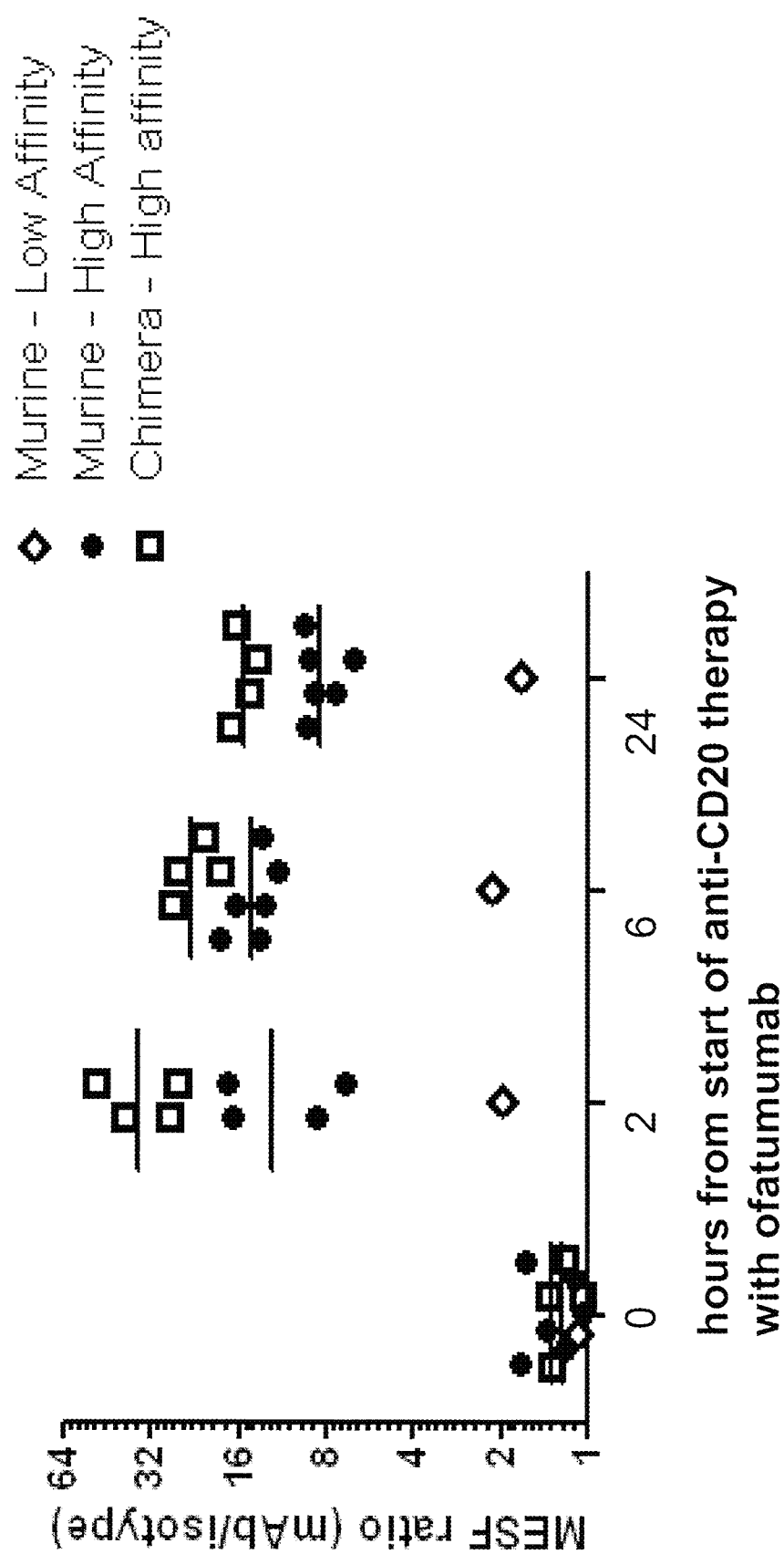

FIG. 3 is a graph showing binding of different anti C3d mAbs to CLL cells from patients being treated with ofatumumab as determined by relative fluorescence intensity, which is the MESF ratio for the mAb versus an isotype control mAb. Binding of both high and low affinity murine mAbs and a high affinity human-mouse chimeric mAb is shown.

FIG. 4 provides graphs of cell count plotted against cell lysis, showing the induction of cell death in CLL cells that were obtained from patients being treated with anti-CD20 therapy and subsequently reacted in vitro with the indicated antibodies ((a) anti-CD20; (b) anti-C3d; (c) anti-CD52) in the presence of normal human serum to test for induction of CDC.

FIG. 5 provides scatter plots showing the induction of cell death in CLL cells that were obtained from patients being treated with anti-CD20 therapy and that were subsequently reacted in vitro with the indicated antibodies ((a) anti-CD20; (b) anti-C3d) in the presence of human NK cells to test for induction of ADCC.

FIG. 6 is a graph showing binding of high affinity C3d mAb to CLL cells from a representative patient being treated with ofatumumab as a function of time during the first week of treatment. C3d on CLL cells is stable as indicated by persistent binding of anti-C3d mAb for up to a week from the start of anti-CD20 therapy.

FIG. 7 is a table of select FDA approved therapeutic antibodies.

FIG. 8 is a graph of resonance units (RU) plotted against time showing antibody binding to immobilized antigen.

Figure 9:
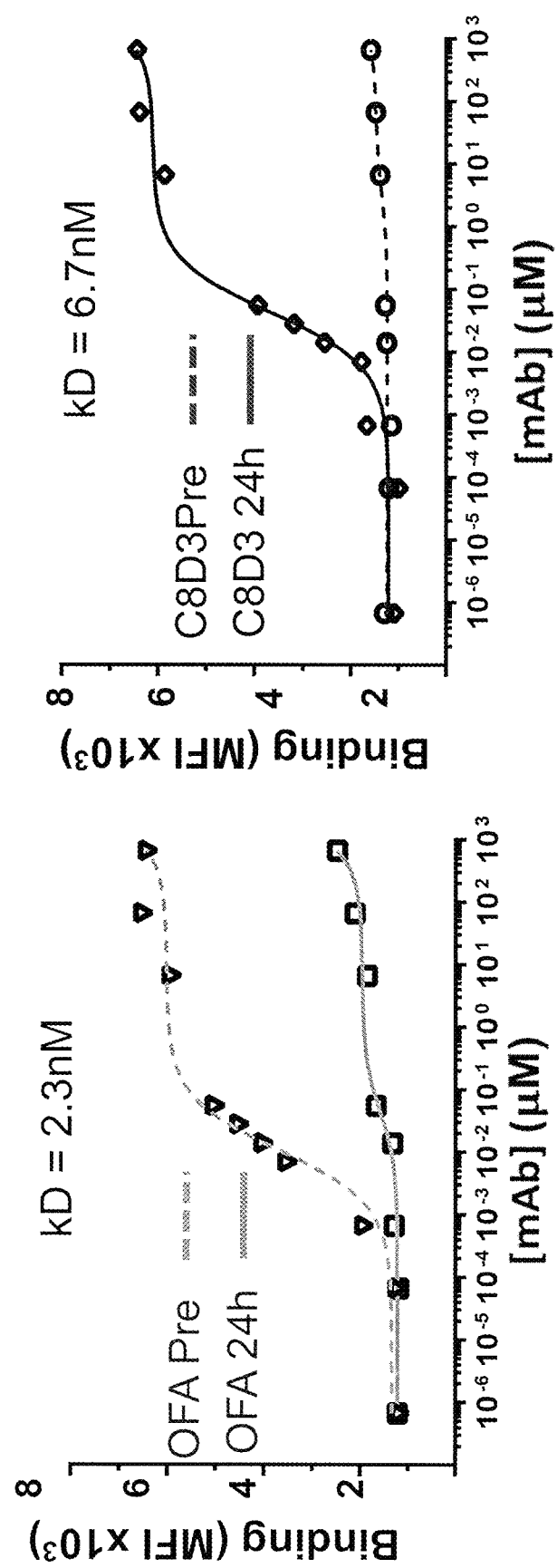

FIG. 9 presents graphs of antibody-antigen binding at various antibody concentrations in the presence and absence of antigen demonstrating antigen avidity of an anti-CD20 and anti-C3d antibody.

Figure 10:
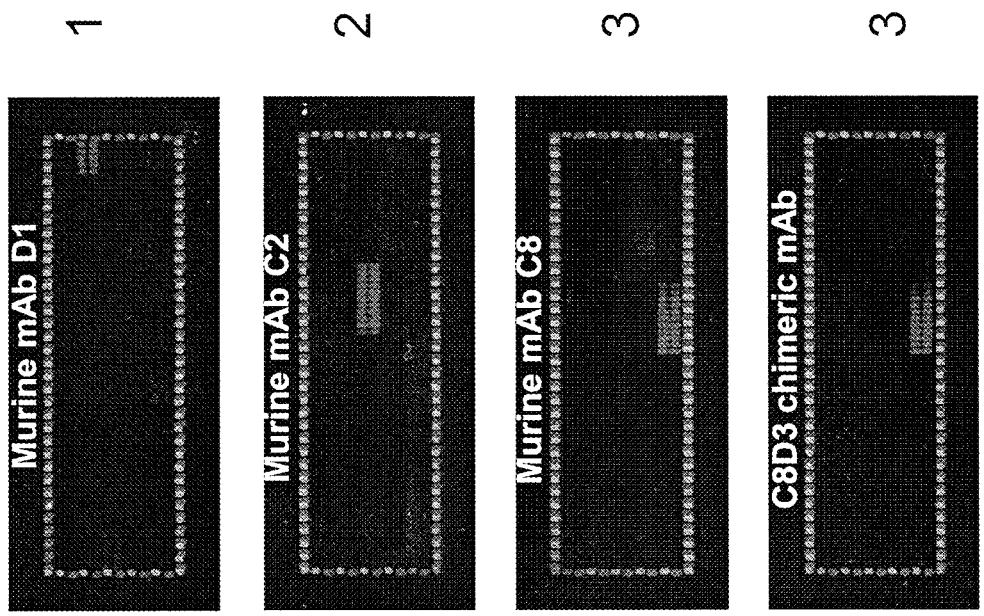

FIG. 10 provides peptide microarray results. Specifically, 15 amino acid (aa) long peptides with 14 aa overlaps were synthesized based on the C3d aa sequence and immobilized in duplicate on microarray chips. The peptide microarrays with the antigen-derived peptides were incubated with antibodies and then stained with a secondary goat anti-human antibody conjugated to DyLight680. The microarrays were read using the LI-COR Odyssey Imaging System and then analyzed using PepSlide® Analyzer software.

Figure 11:
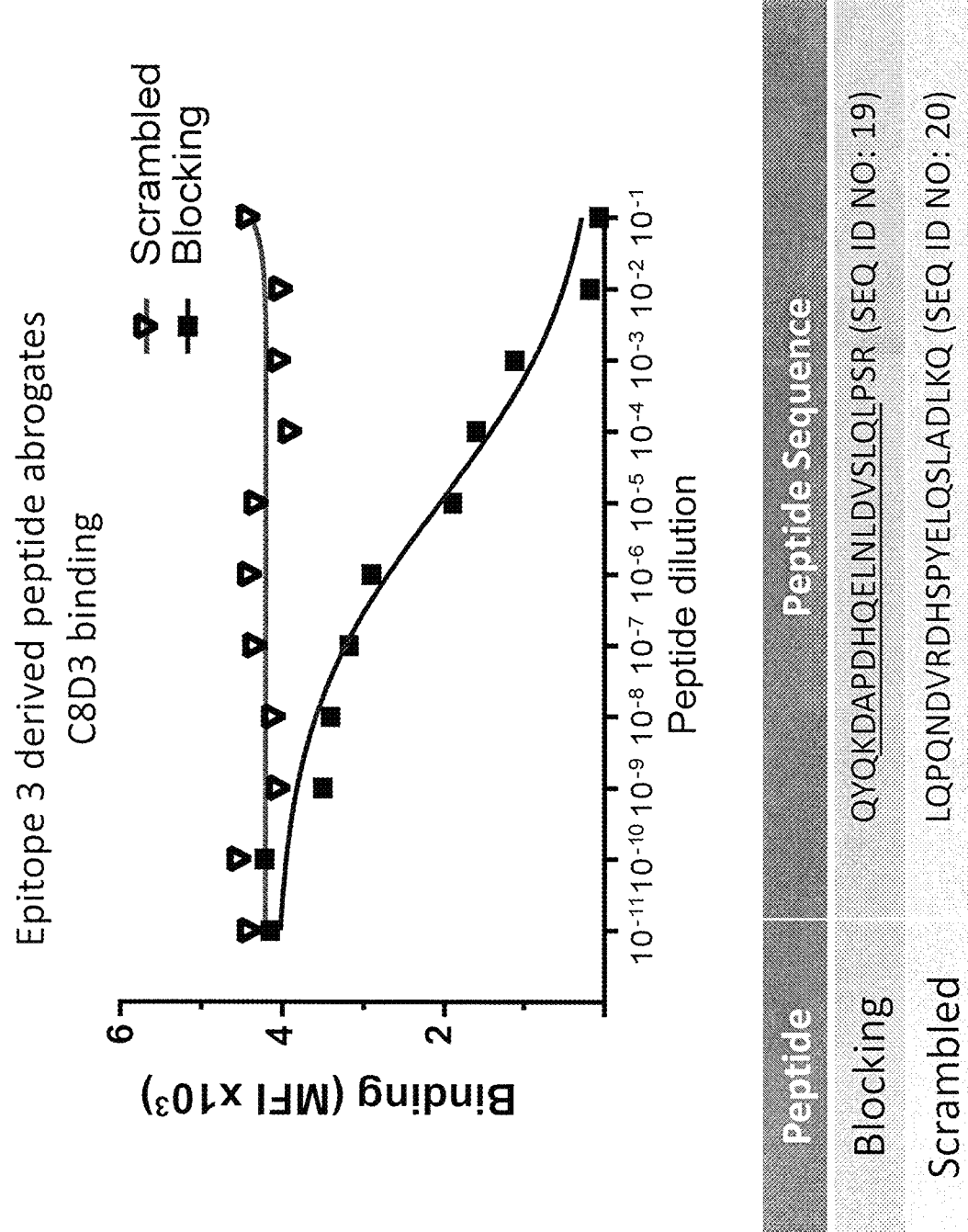

FIG. 11 is a graph of antigen-antibody binding at various concentrations of blocking peptide and scrambled peptide, which shows the potential of the peptide to block antigen-antibody binding.

Figure 12:
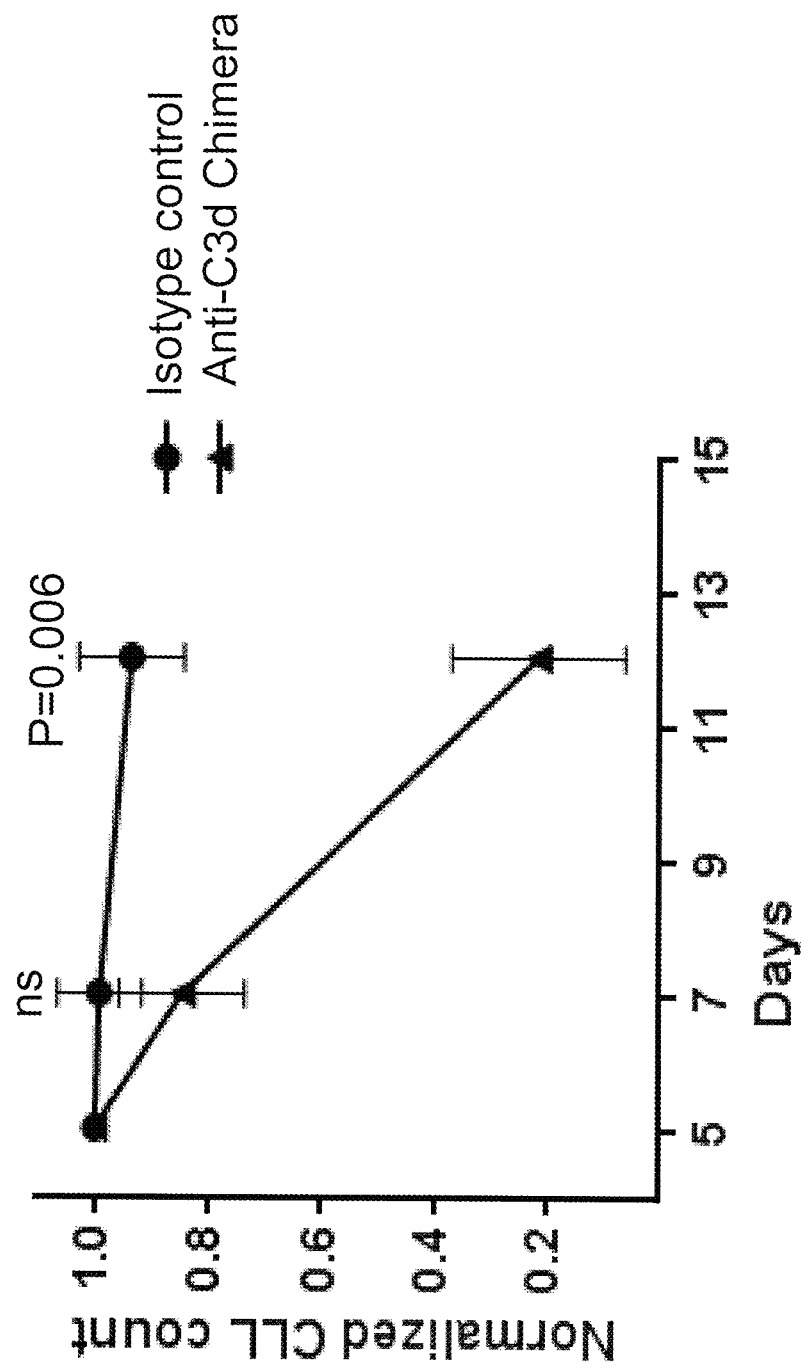

FIG. 12 is a time course of repeated measurements of the number of Chronic Lymphocytic Leukemia (CLL) cells circulating in the blood of CLL xenografted NOD/scid/IL-2R$\gamma^{null}$ mice that were treated with the anti-C3d mouse/human chimeric antibody or an irrelevant antibody of the same isotype (isotype control).

Figure 13:
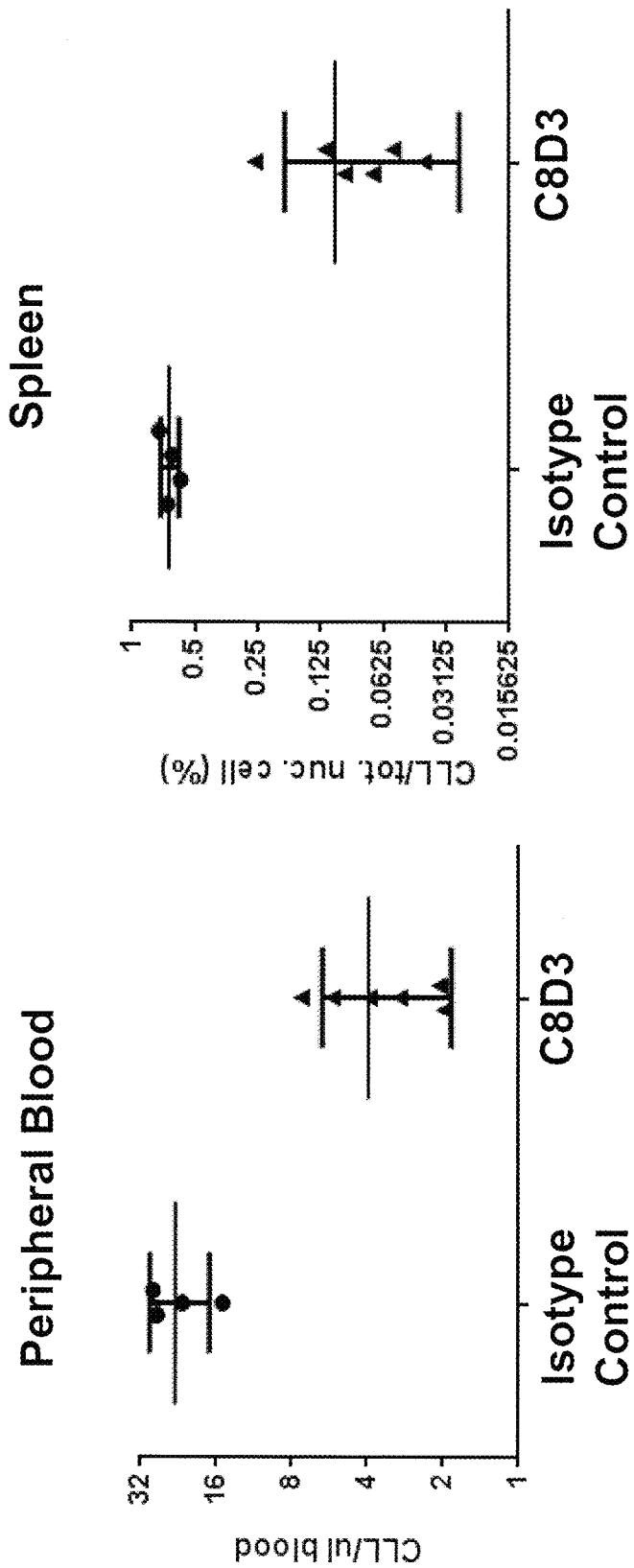

FIG. 13 provides graphs of CLL population in peripheral blood and spleen in an isotype control and anti-C3d antibody (C8D3) treatment group, which show the ability of the anti-C3d mouse/human chimeric antibody to decrease CLL disease burden in the peripheral blood and spleen of xenografted mice compared to the isotype control.

DETAILED DESCRIPTION OF THE INVENTION

Provided is an antibody or antibody fragment immuno-specific for complement protein C3d, and a method of using the antibody or antibody fragment to kill cells having C3d deposited on the surface thereof. C3d is a protein of the complement system. The complement system consists of soluble plasma proteins and is activated upon binding of a mAb to target cells, resulting in the deposition of complement components on the cell surface and formation of the membrane attack complex (MAC), which can kill cells by forming holes in the cell membrane (lysis). The most abundant complement protein is C3. Upon complement activation, C3 is attracted to the cell surface and activated in a proteolytic step, and the product, activated C3b, is deposited on the cell surface followed later by its proteolytic processing to inactive forms, iC3b, C3dg and finally C3d. C3dg and C3d are the final products that remain deposited on the cell membrane for days to weeks, while C3b and iC3b are intermediate products that are further processed within hours. C3d, therefore, provides a stable antigenic target. Without wishing to be bound by any particular theory or mechanism of action, it is believed that the antibodies of the invention bind C3d on the surface of a target cell and, thereby, target the cell for destruction by the host's immune system effector cells (e.g., monocytes, macrophages, NK cells, and neutrophils).

The anti-C3d antibody or antibody fragment is immuno-specific for human C3d complement protein, particularly human C3d complement protein on the surface of an opsonized cancer cell, and/or the C3d precursor protein C3dg, which has a very similar amino acid sequence. In some embodiments, the anti-C3d antibody or antibody fragment has a binding affinity ($K_d$) for human C3d protein of at least 500 nM. Desirably, the anti-C3d antibody or antibody fragment has an affinity for C3d that is sufficiently greater than its affinity for other complement proteins that it does not cross react with other complement proteins, particularly C3, which might otherwise compete with C3d for antibody binding, with the exception that the antibody or antibody fragment may cross-react with C3dg. In some embodiments, the anti-C3d antibody binds an epitope on C3d comprising, or falling within, the amino acid sequence of SEQ ID NO: 16.

The anti-C3d antibody or antibody fragment comprises a variable region that contains complementary determining regions (CDRs), which determine the binding specificity of the antibody or antibody fragment. The variable region may include heavy and light chains.

In one aspect of the invention, the anti-C3d antibody or antibody fragment includes a heavy chain variable region comprising SEQ ID NO: 3 or 4, or sequence with at least about 50% sequence identity thereto (e.g., at least about 60%, 70%, 80%, 90%, 95%, or even 99% sequence identity thereto), as heavy chain complementary determining region-3 (CDRH3). Sequences with at least about 50% sequence identity to SEQ ID NO: 3 or 4 include, for instance, sequences with conservative substitutions or deletions, but which retain binding specificity to the same epitope.

In another aspect, the anti-C3d antibody or antibody fragment is specific for the same epitope to which an antibody comprising heavy chain variable region SEQ ID NO: 8 and light chain variable region SEQ ID NO: 9 binds, or to which an antibody comprising heavy chain variable region SEQ ID NO: 10 and light chain variable region SEQ ID NO: 11 binds. In other words, the anti-C3d antibody or antibody fragment of the invention preferably competes with such an antibody for binding to C3d.

The anti-C3d antibody or antibody fragment can comprise a heavy chain including CDRH3, as described above, and further comprise other CDR regions (e.g., CDRH1 and CDRH2). In some embodiments, the heavy chain comprises SEQ ID NO: 1 as heavy chain complementary determining region-1 (CDRH1); SEQ ID NO: 2 as heavy chain complementary determining region-2 (CDRH2); and/or SEQ ID NO: 3 or 4 as heavy chain complementary determining region-3 (CDRH3); or sequences with at least 50% sequence identity thereto (e.g., at least about 60%, 70%, 80%, 90%, 95%, or even 99% sequence identity thereto). Sequences with at least about 50% sequence identity to the foregoing sequences include, for instance, sequences with conservative substitutions or deletions, but which retain binding specificity to the same epitope.

The anti-C3d antibody or antibody fragment can further comprise a light chain variable region with one, two or three complementary determining regions. In one embodiment, the antibody or antibody fragment comprises: SEQ ID NO: 5 as light chain complementary determining region-1 (CDRL1); SEQ ID NO: 6 as light chain complementary determining region-2 (CDRL2); and/or SEQ ID NO: 7 as light chain complementary determining region-3 (CDRL3); or sequences with at least about 50% sequence identity thereto (e.g., at least about 60%, 70%, 80%, 90%, 95%, or even 99% sequence identity thereto). Sequences with at least about 50% sequence identity to the foregoing sequences include, for instance, sequences with conservative substitutions or deletions, but which retain binding specificity to the same epitope.

According to one aspect of the invention, the anti-C3d antibody or antibody fragment has a light and heavy chain with CDR regions having the following sequences:

SEQ ID NO: 1 as heavy chain complementary determining region-1 (CDRH1);

SEQ ID NO: 2 as heavy chain complementary determining region-2 (CDRH2);

SEQ ID NO: 3 as heavy chain complementary determining region-3 (CDRH3);

SEQ ID NO: 5 as light chain complementary determining region-1 (CDRL1);

SEQ ID NO: 6 as light chain complementary determining region-2 (CDRL2); and

SEQ ID NO: 7 as light chain complementary determining region-3 (CDRL3).

According to another aspect of the invention, the anti-C3d antibody or antibody fragment has having a light and heavy chain with CDR regions having the following sequences:

SEQ ID NO: 1 as heavy chain complementary determining region-1 (CDRH1);

SEQ ID NO: 2 as heavy chain complementary determining region-2 (CDRH2);

SEQ ID NO: 4 as heavy chain complementary determining region-3 (CDRH3);

SEQ ID NO: 5 as light chain complementary determining region-1 (CDRL1);

SEQ ID NO: 6 as light chain complementary determining region-2 (CDRL2); and

SEQ ID NO: 7 as light chain complementary determining region-3 (CDRL3).

The framework regions of the antibody or antibody fragment may be of any suitable type. The antibody or antibody fragment may be chimeric, such that it contains stretches of amino acid sequence from at least two species (e.g., containing constant domains from one species and the variable domains from a second species). The antibody or antibody fragment also can be humanized, such that it has at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence more like a human sequence. The terms "chimeric or humanized" are not mutually exclusive, and encompass, for instance, chimeric antibodies that have been further humanized. The antibody or antibody fragment also can be a fully human antibody, which can be made in a non-human source through genetic engineering techniques.

By way of further illustration, the antibody or antibody fragment may have a heavy chain of SEQ ID NO: 8, and a light chain of SEQ ID NO: 9; or a heavy chain of SEQ ID NO: 10, and a light chain of SEQ ID NO: 11; or a light and/or heavy chain with at least about 50% sequence identity thereto (e.g., at least about 60%, 70%, or 80% sequence identity thereto), or at least about 90% sequence identity thereto (e.g. at least about 91%, 92%, 93%, 94%, 95%, 96%, 97%, 98%, or 99% sequence identity thereto), provided that the heavy and light chains retain the CDR regions as set forth herein. Sequences with at least about 50% or at least about 90% sequence identity to SEQ ID NOs: 8-11 include, for instance, sequences with conservative substitutions or deletions, but which retain binding specificity to the same epitope. The sequences of SEQ ID NOs: 8-11 indicating the CDR regions with underlining are as follows:

C8D3 Heavy chain
(SEQ ID NO: 8)
QAYLQQSGAELVRPGASVKMSCKASGYTFTSYYMEIWVKQTPRQGLEW

IGAIYPGNGDTSYNQKFKGKATLTVDKSSSTAYMQLSSLTSEDSAVYF

CAKGFDYWGQGTTVTVSS

C8D3 Light chain
(SEQ ID NO: 9)
DVVMTQTPLSLPVSLGDQASISCRSSQSLVYSNGNTYLHWYLQKPGQS

PKLLIYKVSNRFSGVPDRFSGSGSGTDFTLKISRVEAEDLGVYFCSQS

THVPYTFGGGTKLEIKR

C6 Heavy chain
(SEQ ID NO: 10)
QAYLQQSGAELVRPGASVKMSCKASGYTFTSYYMEIWVKQTPRQGLEW

IGAIYPGNGDTSYNQKFKGKATLTVDKSSSTAYMQLSSLTSEDSAVYF

CAKYGSGYWGQGTTVTVSS

C6 Light chain
(SEQ ID NO: 11)
DVVMTQTPLSLPVSLGDQASISCRSSQSLVYSNGNTYLHWYLQKPGQS

PKLLIYKVSNRFSGVPDRFSGSGSGTDFTLKISRVEAEDLGVYFCSQS

THVPYTFGGGTKLEIKR

The antibody can be a complete (full) antibody, or an antigen binding antibody fragment. The antibody may be of any immunoglobulin type (e.g., IgG, IgE, IgM, IgD, or IgA), or class (e.g., IgG1, IgG2, IgG3, or IgG4). The antigen binding fragment can be any part of an antibody that has at least one antigen binding site, including, but not limited to, IgGACH2, Fab, F(ab')2, Fv, dsFv, scFv, scFv2CH3, scFv4, scFv3, scFv2, scFv-Fc, diabodies, triabodies, bis-scFvs, (scFv)2, fragments expressed by a Fab expression library, domain antibodies, VhH domains, V-NAR domains, VH domains, VL domains, and the like. Antibody fragments of the invention, however, are not limited to these exemplary types of antibody fragments. Furthermore, the antibody or antibody fragment can be engineered to have various configurations known in the art. For example, the antibody or antibody fragment can be linked to a synthetic molecule with the following domains: a spacer or hinge region (e.g., a CD28, CD28, or IgG hinge), a transmembrane region (e.g., a transmembrane canonical domain), and/or an intracellular T-cell receptor (TCR) signaling domain, thereby forming a T-body or chimeric antigen receptor (CAR). Intracellular TCR signaling domains that can be included in a T-body (or CAR) include, but are not limited to, CD3ζ, FcR-γ, and Syk-PTK signaling domains as well as the CD28, 4-1BB, and CD134 co-signaling domains. Methods for constructing T-cells expressing a T-body (or CAR) are known in the art. See, e.g., Marcu-Malina et al., *Expert Opinion on Biological Therapy*, 9: 539-564 (2009).

The antibody or antibody fragment includes antibodies that have been mutated or otherwise modified to modulate function. For instance, the antibody or antibody fragment can comprise a mutation of the Fc-region of a human IgG1 heavy chain to enhance effector function, as described in WO 2013/004842. Or, the antibody can be glycoengineered, for instance, to enhance monocyte/macrophage-mediated phagocytosis and cytotoxicity (see, e.g., Herter et al., *J. Immunol.*, 192(5): 2252-60 (2014). The antibody or antibody fragments described herein can be modified in any of various other ways known in the art without departing from the scope of the invention.

A domain antibody comprises a functional binding unit of an antibody, and can correspond to the variable regions of either the heavy (VH) or light (VL) chains of antibodies. A domain antibody can have a molecular weight of approximately 13 kDa, or approximately one-tenth of a full antibody. Domain antibodies may be derived from full antibodies such as those described herein.

The antigen binding fragments in some embodiments are monomeric or polymeric, bispecific or trispecific, bivalent or trivalent. Antibody fragments that contain the antigen binding, or idiotype, of the antibody molecule may be generated by techniques known in the art. For example, such fragments include, but are not limited to, the F(ab')2 fragment which may be produced by pepsin digestion of the antibody molecule; the Fab' fragments which may be generated by reducing the disulfide bridges of the F(ab')2 fragment, and the two Fab' fragments which may be generated by treating the antibody molecule with papain and a reducing agent.

A single-chain variable region fragment (scFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al. (eds.), Immunobiology, 5th Ed., Garland Publishing, New York, N.Y. (2001)). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., Biomol. Eng. 2001 18:95-108, (2001) and Todorovska et al., J. Immunol. Methods, 248:47-66 (2001).

Bispecific antibodies (bscAb) are molecules comprising two single-chain Fv fragments joined via a glycine-serine linker using recombinant methods. The V light-chain (VL) and V heavy-chain (VH) domains of two antibodies of interest in exemplary embodiments are isolated using standard PCR methods. The VL and VH CDNA'S obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both applications of which are incorporated herein by reference in their entirety. The multispecific antibody can be configured as a BiTE or DART. BiTEs consist of a single polypeptide displaying two antigen-binding specificities through cognate heavy and light chain variable domains. BiTEs have one N-terminus and one C-terminus. In DARTs, cognate heavy and light chain variable domains are on two separate polypeptides that associate and are stabilized by a C-terminal disulfide bridge. Thus, DARTs have 2 N-termini and 2 C-termini.

The anti-C3d antibody can be made by any suitable technique. The antibody is an engineered antibody produced by synthetic, recombinant, or other manufacturing techniques. Suitable methods of making engineered antibodies are known in the art. For instance, a polyclonal antibody can be prepared by immunizing an animal with an immunogen (e.g., C3d) and collecting antisera from that immunized animal. A wide range of animal species can be used for the production of antisera. In some aspects, an animal used for production of antisera is a non-human animal including rabbits, mice, rats, hamsters, goat, sheep, pigs or horses. Polyclonal antisera may be obtained, after allowing time for antibody generation, simply by bleeding the animal and preparing serum samples from the whole blood. The polyclonal antibodies, thus, obtained can then be screened for specific desired antibodies (e.g., antibodies of the invention).

Monoclonal antibodies may be prepared using any technique which provides for the production of antibody molecules by continuous cell lines in culture. Several hybridoma methods are known in the art (e.g., Koehler and Milstein, *Nature* 256: 495-497, 1975); Kosbor et al., *Immunol Today* 4:72, 1983; Cote et al., *Proc Natl Acad Sci* 80: 2026-2030, 1983); Cole et al., *Monoclonal Antibodies and Cancer Therapy*, Alan R Liss Inc, New York N.Y., pp 77-96, (1985); Harlow and Lane (eds.), *Antibodies: A Laboratory Manual*, CSH Press (1988), and CA. Janeway et al. (eds.), *Immunobiology*, 5th Ed., Garland Publishing, New York, N.Y. (2001); Haskard and Archer, *J. Immunol. Methods*, 74(2), 361-67 (1984); Roder et al., *Methods Enzymol.*, 121, 140-67 (1986); Huse et al., *Science*, 246, 1275-81 (1989)). Other known antibody production techniques can also be used, such as by producing human antibodies in non-human animals (e.g., U.S. Pat. Nos. 5,545,806, 5,569,825, and 5,714,352, and U.S. Patent Application Publication No. 2002/0197266 A1), screening methods (e.g., Orlandi et al., *Proc Natl Acad Sci* 86: 3833-3837 (1989), and Winter G and Milstein C, *Nature* 349: 293-299, (1991); phage display methods (e.g., Sambrook et al. (eds.), *Molecular Cloning, A Laboratory Manual*, 3 Edition, Cold Spring Harbor Laboratory Press, New York (2001); use of transgenic mice (e.g., U.S. Pat. Nos. 5,545,806 and 5,569,825);

Methods for generating engineered and humanized antibodies are well known in the art (e.g., Janeway et al. (eds.), *Immunobiology*, 5th Ed., Garland Publishing, New York, N.Y. (2001); U.S. Pat. Nos. 5,225,539, 5,585,089, 5,693, 761, and 5,693,762; European Patent No. 0239400 B1, and United Kingdom Patent No. 2188638; Jones et al., Nature 321: 522-525 (1986); Riechmann et al., *Nature*, 332: 323-327 (1988) and Verhoeyen et al., Science 239:1534-1536 (1988); U.S. Pat. No. 5,639,641; Pedersen et al., J. Mol. Biol, 235, 959-973 (1994); and Owens and Young, *J. Immunol. Meth.*, 168:149-165 (1994).

Techniques developed for the production of "chimeric antibodies", the splicing of mouse antibody genes to human antibody genes to obtain a molecule with appropriate antigen specificity and biological activity, can be used (Morrison et al., *Proc Natl Acad Sci* 81: 6851-6855, 1984; Neuberger et al., *Nature* 312: 604-608, 1984; Takeda et al., *Nature* 314: 452-454 (1985)). Also, techniques described for the production of single chain antibodies can be employed (U.S. Pat. No. 4,946,778).

Chemically constructed bispecific antibodies may be prepared by chemically cross-linking heterologous Fab or F(ab')2 fragments by means of chemicals such as heterobifunctional reagent succinimidyl-3-(2-pyridyldithiol)-propionate (SPDP, Pierce Chemicals, Rockford, 111). The Fab and F(ab')2 fragments can be obtained from intact antibody by digesting it with papain or pepsin, respectively (Karpovsky et al., *J. Exp. Med.* 160:1686-701, 1984; Titus et al., *J. Immunol.*, 138:4018-22, 1987).

Methods of testing antibodies for the ability to bind to C3d, regardless of how the antibodies are produced, are known in the art and include any antibody-antigen binding assay, such as, for example, radioimmunoassay (MA), ELISA, Western blot, immunoprecipitation, and competitive inhibition assays (see, e.g., Janeway et al. (eds.), Immunobiology, 5th Ed., Garland Publishing, New York, N.Y. (2001); and U.S. Patent Application Publication No. 2002/0197266 A1).

The antibody can be isolated. The term "isolated" as used herein encompasses compounds or compositions that have been removed from a biological environment (e.g., a cell, tissue, culture medium, body fluid, etc.), or otherwise increased in purity to any degree (e.g., isolated from a synthesis medium). Isolated compounds and compositions, thus, can be synthetic or naturally produced.

Also provided is a nucleic acid encoding the anti-C3d antibody as described herein, which can be used to produce the antibody by expressing the nucleic acid in a cell. The nucleic acid can comprise any suitable nucleotide sequence that encodes the antibody or portion thereof (e.g., CDRs, framework regions, and other parts of the antibody or antibody fragment). A nucleic acid comprising the desired nucleotide sequence can be constructed based on chemical synthesis and/or enzymatic ligation reactions using procedures known in the art (e.g., The nucleic acids in some aspects are constructed based on chemical synthesis and/or enzymatic ligation reactions using procedures known in the art. See, for example, et al. (eds.), Molecular Cloning, A Laboratory Manual, 3 Edition, Cold Spring Harbor Laboratory Press, New York (2001). Examples of nucleotide sequences encoding the variable regions of antibodies of the invention include SEQ ID NOs: 12-15.

Also provided is a recombinant expression vector comprising the nucleotide sequence encoding the antibody or antibody fragment. The recombinant expression vector of the invention can be any suitable recombinant expression vector, and can be used to transform or transfect any suitable host. Suitable vectors include those designed for propagation and expansion or for expression or both, such as plasmids and viruses. Examples of vectors include the pUC series (Fermentas Life Sciences), the pBluescript series (Stratagene, La Jolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λvTIO, λvTI 1, AZapII (Stratagene), EMBL4, and λNMI 149, also can be used. Examples of plant expression vectors include pBIO1, pBI101.2, pBI101.3, pBI121 and pBIN19 (Clontech). Examples of animal expression vectors include pEUK-Cl, pMAM and pMAMneo (Clontech). The recombinant expression vector can be a viral vector, e.g., a retroviral vector.

Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector can comprise regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector may include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the presently disclosed expression vectors include, for instance, neomycin/G418 resistance genes, hygromycin resistance genes, histidinol resistance genes, tetracycline resistance genes, and ampicillin resistance genes.

The recombinant expression vector can comprise a native or non-native promoter operably linked to the nucleotide sequence encoding the polypeptide (including functional portions and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The recombinant expression vectors of the invention can be prepared using standard recombinant DNA techniques described in, for example, Sambrook et al., supra.

The nucleic acid or vector can be in a host cell. The host cell can be any type of cell. The host cell in some aspects is a eukaryotic cell, e.g., plant, animal, fungi, or algae, especially a human cell, or can be a prokaryotic cell, e.g., bacteria or protozoa. The host cell in some aspects is a cultured cell or a primary cell, i.e., isolated directly from an organism, e.g., a human. The host cell in some aspects is an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like.

Thus, the invention further provides eukaryotic or non-eukaryotic cells that have been recombinantly engineered to produce an antibody or antibody fragment of the invention. The cells can be targeted immune cells that are engineered to recombinantly express the anti-C3d antibody or antibody fragment as a cell surface reactive antibody or antibody fragment, such as a T-body or chimeric antigen receptor (CAR). For example, cell can be a T-cell engineered to express an antibody or antibody fragment of the invention (e.g., an scFv, scFv-Fc, or (scFv)2) linked to a spacer or hinge region (e.g., a CD28, CD28, or IgG hinge), a transmembrane region (e.g., a transmembrane canonical domain), and an intracellular T-cell receptor (TCR) signaling domain, thereby forming a T-body or CAR. Intracellular TCR signaling domains that can be included in a T-body (or CAR) include, but are not limited to, CD3ζ, FcR-γ, and Syk-PTK signaling domains as well as the CD28, 4-1BB, and CD134 co-signaling domains. Methods for constructing T-cells expressing a T-body (or CAR) are known in the art. See, e.g., Marcu-Malina et al., *Expert Opinion on Biological Therapy*, 9: 539-564 (2009).

The anti-C3d antibody or fragment thereof may be conjugated or fused to another molecule, or to a support, optionally by way of a linker molecule. Any of a variety of molecules can be conjugated or fused to the anti-C3d antibody for various purposes, including diagnostic, marking or tracing, therapeutic, or recovery/purification purposes. Examples of such other molecules include, without limitation, detectable labels, affinity tags, and therapeutic agents, including cytotoxic, cytostatic, or antiangiogenic agents and radioisotopes. Therapeutic agents can be, for example, a plant, fungal, or bacterial molecules (e.g., a protein toxin), small molecule chemotherapeutics, or biological therapeutics. Examples of therapeutic molecules include, for instance, a maytansinoid (e.g., maytansinol or DM1 maytansinoid), a taxane, a calicheamicin, an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas, or thiotepa); an antimitotic agent (e.g., a *vinca* alkaloid like vincristine or taxoid such as paclitaxel or docetaxel); a topoisomerase inhibitor (for example, etoposide, and teniposide, amsacrine, or topotecan); a cell cycle inhibitor (for example, a flavopyridol); a microbtubule agent (e.g., an epothilone, discodermolide analog, or eleutherobin analog); a proteosome inhibitor or a topoisomerase inhibitor such as bortezomib, amsacrine, etoposide, etoposide phosphate, teniposide, or doxorubicin; a radioisotope including yttrium ($^{90}$Y), lutetium ($^{177}$Lu), actinium ($^{225}$Ac), praseodymium, astatine ($^{111}$At), rhenium ($^{186}$Re), bismuth ($^{212}$Bi or $^{213}$Bi), and rhodium ($^{188}$Rh); an antiangiogenic agent such as linomide, bevacuzimab, angiostatin, and razoxane; an antibody or antibody fragment other than an anti-C3d antibody or antibody fragment, such as rituximab or bevacuzimab. Labels can be useful in diagnostic applications and can include, for example, radiolabels contrast agents. A contrast agent can be a radioisotope label such as iodine ($^{131}$I or $^{125}$I), indium ($^{111}$In), technetium ($^{99}$Tc), phosphorus ($^{32}$P), carbon ($^{14}$C), tritium ($^{3}$H), other radioisotope (e.g., a radioactive ion), or a therapeutic radioisotope listed above. Additionally, contrast agents can include radiopaque materials, magnetic resonance imaging (MM) agents, ultrasound imaging agents, and any other contrast agents suitable for detection by a device that images an animal body; as well as a fluorescent label, a biologically active enzyme label, a luminescent label, or a chromophore label.

Methods of conjugating or fusing such other molecules to an antibody without interfering with the binding of the antibody to its target antigen are known in the art. Recombinant engineering and incorporated selenocysteine (e.g., as described in International Patent Application Publication WO 2008/122039) can be used to conjugate a synthetic molecule. Other methods of conjugation can include covalent coupling to native or engineered lysine side-chain amines or cysteine side-chain thiols. See, e.g., Wu et al., *Nat. Biotechnol.*, 23: 1137-1146 (2005).

The anti-C3d antibody or antibody fragment can be part of a composition, particularly a pharmaceutical composition, comprising the anti-C3d antibody or fragment and a carrier. Any carrier suitable for proteins, particularly antibodies, can be used. A pharmaceutically acceptable carrier is preferred. The term "pharmaceutically acceptable carrier" as used herein means one or more compatible solid or liquid fillers, diluents, other excipients, or encapsulating substances which are suitable for administration into a human or veterinary patient. The carrier can be co-mingled with the one or more active components without substantially impairing the desired pharmaceutical efficacy. Pharmaceutically acceptable materials generally are capable of administration to a patient without the production of significant undesirable physiological effects. The pharmaceutical composition can contain suitable buffering agents, preservatives, and other components typically used in pharmaceutical formulations, particularly therapeutic antibody formulations. The pharmaceutical composition can be presented in a unit dosage form suitable for the desired route of administration (e.g., oral, parenteral, etc).

The anti-C3d antibody can be used for any purpose, such as for labeling opsonized cells, or targeting opsonized cells for delivery of a therapeutic agent. Thus, the invention provides, in one aspect, a method of labeling a cell comprising C3d complement protein on the surface thereof (e.g., an opsonized cell) by contacting the cell with an anti-C3d antibody as described herein that contains a detectable label. According to another aspect, the invention provides a method of delivering a therapeutic agent to a cell comprising C3d complement protein on the surface thereof (e.g., an opsonized cell) by contacting the cell with an anti-C3d antibody as described herein attached to a therapeutic agent. All aspects of the anti-C3d antibody attached to a detectable label or therapeutic agent are as previously described.

The anti-C3d antibody is believed to be particularly useful for eliminating cells, especially cancer cells, by binding to C3d surface proteins on such cells and causing their destruction by cell lysis or phagocytosis. Thus, the invention further provides a method of killing cancer cells comprising C3d complement protein on the surface thereof (e.g., a C3d opsonized, viable cancer cell) by contacting the cell with the anti-C3d antibody described herein, wherein the immune system of the subject is recruited to kill the cancer cell. Alternatively, the method can comprise administering anti-C3d antibody conjugated to a cytotoxic agent to the subject, wherein the anti-C3d antibody targets cancer cells with C3d on the surface and the cytotoxic agent kills the cells. In this respect, killing cancer cells is not limited to direct killing of cancer cells, but includes any method or mechanism by which a living, viable cancer cell may be eliminated from a host as a result of contacting the cancer cell with an antibody of the invention.

The cell may be any type of cell having a C3d surface protein. Typically, the cell will be a cancer cell or other pathogenic cell having a C3d surface protein (e.g., an opsonized cancer cell or other pathogenic cell). The cancer cell may acquire C3d surface proteins through binding of a mAb to molecules on the surface of the cancer cell. The cancer cell can be a cell of any type of cancer that has a C3d protein on the cell surface. Non-limiting examples of specific types of cancers include cancer of the head and neck, eye, skin, mouth, throat, esophagus, chest, bone, lung, colon, sigmoid, rectum, stomach, prostate, breast, ovaries, uterus (e.g., endometrium), kidney, liver, pancreas, brain, intestine, heart or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., Harrison's Principles of Internal Medicine, Eugene Braunwald et al., eds., 491-762 (15th ed. 2001). In some embodiments, the cancer cell is from gut, colon, lung, breast, head, neck, pancreas, ovary, endometrium, or brain tissue; or is a plasma cell or a myeloid cell.

The methods of the invention are believed to be especially useful to target a cancer cell that has lost a therapeutic target antigen through trogocytosis. In a specific embodiment, the cell is a chronic lymphocytic leukemia cell, and the method may be performed on a patient with chronic lymphocytic leukemia. In another embodiment, the cancer cell is a B-cell expressing CD20, and the method may be performed on a patient with CD20+B-cell malignancy. In yet another embodiment, the cell is from a cancer treated with a mAb (examples of mAbs in clinical use are given in FIG. 7) and the method may be performed on a patient in need of treatment for such a cancer.

Any of the foregoing methods may further comprise inducing the formation of C3d on the surface of the cell. This may be accomplished by contacting the cell with an agent that activates the complement system, such as by opsonizing the cell by contact with an antibody or antigen-binding fragment thereof that binds to a surface protein on the cell other than C3d. The antibody that binds to a cell-surface protein other than C3d can be, for example, a therapeutic antibody or antibody fragment. Examples include an anti-CD20 antibody or antibody fragment (e.g., rituximab, ofatumumab, ocrelizumab, veltuzumab, obinutuzumab (GA-101), PRO131921, or ocaratuzumab (AME-133)), an anti-CD33 antibody or antibody fragment (e.g., gemtuzumab, or lintuzumab), an anti-CD38 antibody (e.g., daratumumab), an anti-CD52 antibody (e.g., Alemtuzumab), an anti-ERBB2 antibody (e.g., trastuzumab), and an anti-EGFR antibody (e.g., cetuximab, or panitumumab). FIG. 7 also provides examples of FDA approved monoclonal antibodies targeting cancer cell surface antigens.

The anti-C3d antibody or antibody fragment and the antibody or antibody fragment that binds to a surface protein on the cell other than C3d can be separate molecules or they can be part of the same multi-specific antibody. Thus, for instance, a multi-specific antibody having immunospecificity for C3d and a different cell-surface protein (e.g., CD20, CD33, CD38, etc.) can be used to both induce the complement cascade resulting in C3d formation on the cell surface and to bind C3d once formed. If separate antibodies or antibody fragments are used to induce C3d formation on the cell surface and bind to C3d once formed, they can be administered to the subject simultaneously or sequentially in any order, though typically the antibody that binds to a cell-surface protein other than C3d will be administered before or approximately at the same time as the anti-C3d antibody.

In accordance with any of the foregoing methods, the cell may be in vitro or in vivo. For instance, the cell may be in a patient, who may be afflicted with a disease. When the cell is in the patient, the cell may be contacted by the anti-C3d antibody or other agent by administering the antibody or other agent to the patient. If the patient is afflicted with a disease, the administration of the anti-C3d antibody and/or other agents can, according to certain embodiments, treat the disease by reducing one or more symptoms or characteristics of the disease. The patient can be a patient treated with a therapy (e.g., monoclonal antibody therapy, particularly anti-CD20 monoclonal antibody therapy, such as with rituximab or ofatumumab) resulting in C3d deposition on the cancer cells. In one embodiment trogocytosis may lead to loss of the CD20 antigen and anti-C3d mAb can be used to target these cells. In a second embodiment anti CD20 therapy leads to C3d deposition but incomplete killing of the cancer cell, that can then be eliminated by anti-C3d mAb alone, or by the combination of the anti CD20 mAb with the anti-C3d mAb. In one embodiment anti-CD20 mAb is combined with anti-C3d mAb for the treatment of CD20 positive B-cell malignancies.

Thus, for instance, the method may comprise administering to a patient, simultaneously or sequentially, an anti-C3d antibody as described herein and an agent that induces formation of C3d on the surface of a cell (e.g., a monoclonal antibody, such as an anti-CD20 antibody like rituximab, ofatumumab, ocrelizumab, Veltuzumab, obinutuzumab (GA-101), PRO131921, ocaratuzumab (AME-133) or any antibody or antibody fragment to a cell surface antigen described herein, or other opsonizing agent). The cell is particularly a pathogenic cell such as a cancer cell. By way of further example, the cell can be a chronic lymphocytic leukemia cell, and the patient can have chronic lymphocytic leukemia.

The anti-C3d antibody and agent that induces formation of C3d on the surface of a cell can be administered simultaneously as separate compositions or as a single composition, or the two agents can be administered sequentially in any order. When administered sequentially, the timeframe of administration is not particularly limited, but the anti-C3d antibody and agent that induces C3d formation on the cell will typically be administered within several minutes (e.g., within 10, 20, 30, 40, or 50 minutes) or within several hours (e.g., within 1, 2, 4, 8, 12, or 24 hours), or within several days (e.g 1, 2, 5, 7), or within several weeks (e.g. 1, 2, 3, 4) of one another.

Also provided herein is a short (about 50 amino acids or less) polypeptide comprising an anti-C3d epitope of SEQ ID NO: 16, 17, or 18, or a combination thereof. The polypeptide can have fewer than 50 amino acids, such as about 45 amino acids or fewer, about 40 amino acids or fewer, about 35 amino acids or fewer, about 30 amino acids or fewer, about 25 amino acids or fewer, or about 20 amino acids or fewer. In some embodiments, the polypeptide can consist essentially of, or consist of, SEQ ID NO: 16, 17, or 18, or combination thereof. If the polypeptide comprises amino acid residues flanking the sequence of SEQ ID NO: 16, 17, or 18, or combination thereof, the flanking residues can have any suitable sequence provided they do not interfere with the binding of the epitope sequence to an antibody targeting the epitope. The flanking sequences can be, for instance, the sequences that flank SEQ ID NOs: 16, 17, or 18, in the native C3d protein, such that the polypeptide is a fragment of C3d comprising SEQ ID NO: 16, 17, or 18, or a combination of such fragments joined together.

In yet another embodiment, the polypeptide can comprise, consist essentially of, or consist of a fragment of SEQ ID NO: 16, 17, or 18, or a combination of such fragments, large enough to facilitate binding of an antibody (e.g., an anti-C3d antibody as described herein). Thus, the fragment will typically comprise at least about 5 contiguous amino acids, such as at least about 10 contiguous amino acids, of SEQ ID NO: 16, 17, or 18.

The polypeptide can be bound to a support, directly or via a linker molecule. The support can be any type of support (e.g., solid supports, such as a bead or plate), particular a support useful in biopanning techniques, such as panning a phage display library.

The polypeptide can be used for any suitable purpose. For instance, the polypeptide can be used to screen for, select, or produce anti-C3d antibodies. Thus, provided herein is a method of screening, selecting, or producing anti-C3d antibodies by contacting one or more antibodies or antibody fragments (e.g., a library, such as a phage display library) with the polypeptide and selecting an antibody or antibody fragment that binds to the polypeptide. The method can comprise repeatedly performing the contacting and selection steps (e.g., panning) using the polypeptide and selecting those antibodies or antibody fragments that exhibit the greatest affinity for the polypeptide. Specific techniques for panning antibody libraries using polypeptides are known in the art. For instance, the polypeptide can be used in conjunction with panning phage display libraries.

The polypeptides also can be used to elicit an immunogenic response in a mammal. Thus, provided herein is a method of eliciting an immunogenic response in a mammal by administering the polypeptide to a mammal. The immunogenic response can be for any purpose, such as for therapy or for the production and subsequent harvesting of antibodies.

Also provided is a nucleic acid encoding the polypeptide, optionally in a vector. The vector can be any of those described herein with respect to the nucleic acid encoding the antibody of the invention.

The following examples further illustrate the invention but, of course, should not be construed as in any way limiting its scope.

Example 1

This example demonstrates the production of an antibody of the present invention.

HTP mice were injected with C3d protein and antibodies were harvested. Nine hybridoma clones were identified that produce antibodies with the desired selectivity for C3d. Sequence analysis (nucleotide sequencing and for select mAbs protein shot gun sequencing) revealed 4 unique antibody clones:

The C6 and C8D3 clones were further studied. The CDR regions of the two clones are presented below:

| Heavy Chain | CDRH1 | CDRH2 | CDRH3 |
|---|---|---|---|
| C8D3 | GYTFTSYY (SEQ ID NO: 1) | IYPGNGDT (SEQ ID NO: 2) | AKGFD (SEQ ID NO: 3) |
| C6 | GYTFTSYY (SEQ ID NO: 1) | IYPGNGDT (SEQ ID NO: 2) | AKYGSG (SEQ ID NO: 4) |

| Light Chain | CDRL1 | CDRL2 | CDRL3 |
|---|---|---|---|
| C8D3 | QSLVYSNGNTY (SEQ ID NO: 5) | KVS (SEQ ID NO: 6) | SQSTHVPYT (SEQ ID NO: 7) |
| C6 | QSLVYSNGNTY (SEQ ID NO: 5) | KVS (SEQ ID NO: 6) | SQSTHVPYT (SEQ ID NO: 7) |

In vitro binding studies of the above clones to ARH77 cells opsonized with complement in vivo showed that the antibodies are not competed away by native C3 present in human plasma (FIG. 2). For these studies, ARH77 cells (treated overnight with RTX+NHS) in 50% FBS or NHS with 10 mM EDTA, and 5 ug/ml mAb binding to CLL cells in 50% FBS or NHS with 10 mM EDTA, were used.

Binding studies show that the mouse/human chimeric anti C3d mAb C8D3 retains the specificity of its murine parental clone and binds C3d with high affinity (FIGS. 3 and 8).

Example 2

This example shows that an antibody of the invention can eliminate anti-CD20 mAb resistant cells by CDC.

Figure 1A:
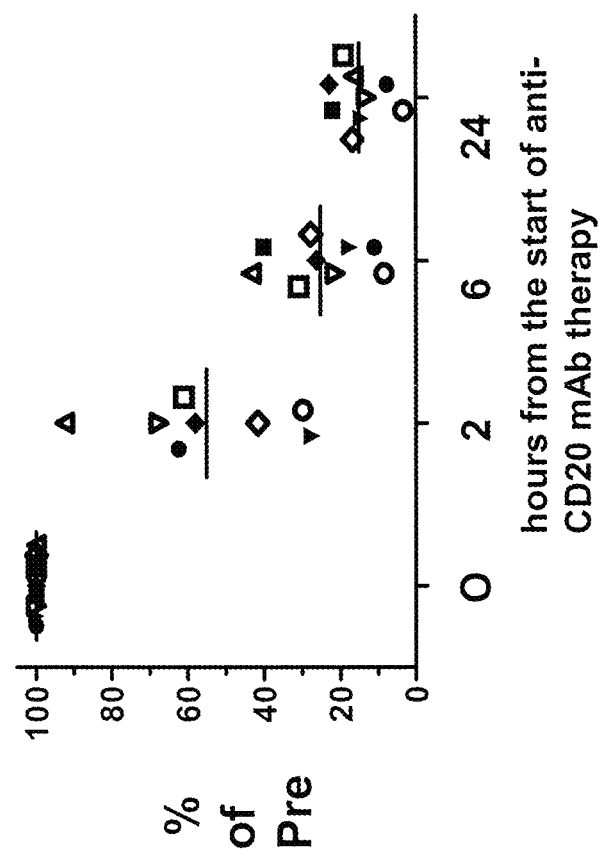
FIG. 1A is a graph of CD20 expression on tumor cells obtained from the peripheral blood of patients with CLL being treated with anti-CD20 therapy (expressed as a percentage of CD20 expression pretreatment (% of Pre)) plotted against hours post-start of treatment. The graph illustrates the loss of CD20 expression on the tumor cells over time.
Figure 1B:
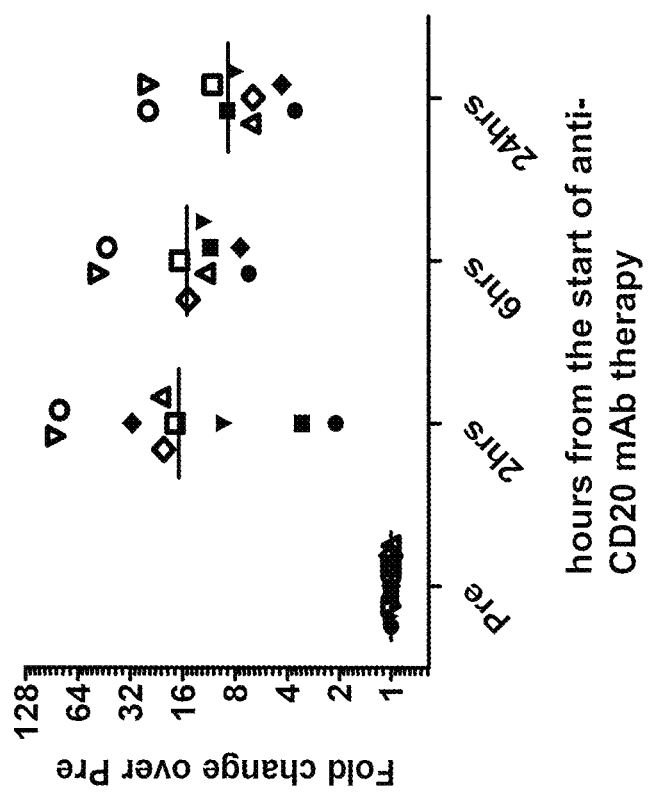
FIG. 1B is a graph showing C3d deposition on tumor cells over the course of anti CD20 therapy, expressed as a fold-change from C3d levels pre-treatment, plotted against the number of hours post-start of anti-CD20 mAb therapy.

As shown in FIGS. 1A-1C, CLL cells treated with anti-CD20 mAb lose CD20-antibody complexes through a process known as trogocytosis and, as a result, can escape cell lysis or phagocytosis despite monoclonal antibody treatment. By binding to C3d complement protein, the antibodies of the present invention can target these escaped cells.

CLL cells obtained from patients treated with anti-CD20 mAb were exposed to antibody (anti-CD20 (ofatumumab), anti-CD52 (alemtuzumab), or anti-C3d (chimeric C8D3) in vitro in the presence of human complement. Ramos cells were pretreated overnight with 10 ug/ml OFA in 10% NHS. Then various concentrations of antibody were added for 2 hrs with fresh NHS (10% final concentration). The results are presented in FIG. 4.

The results show that the antibodies of the present invention, but not anti-CD20 mAb, promote killing of the anti-CD20 mAb resistant cells by making use of immune effector functions such as complement. Furthermore, the anti-CD20 mAb resistant cells can be lysed equally well by anti-C3d (chimeric C8D3) and anti-CD52 (alemtuzumab) mAb s.

Example 3

This example shows that ADCC is a second mechanism by which antibodies of the invention selectively kills CLL

| Clone | Affinity | Type | HV gene | HD gene | HJ gene | HV CDR3 | LV gene |
|---|---|---|---|---|---|---|---|
| B7 | + | IgG1, K | 1-72 * 01 | 2-3 * 01 | 4 * 01 | AREG? | ND |
| C2 | + | IgG2a, λ | 1-53 * 01 | 1-1 * 01 | 4 * 01 | ARFITTVGF | ND |
| C6 | +++ | IgG1, K | 1-12 * 01 | 1-1 * 01 | 2 * 01 | AKYGSG | K1-110 * 01 |
| C8 | +++ | IgG1, K | 1-12 * 01 | 2-4 * 01 | 2 * 01 | AKGFD | K1-110 * 01 |
| D3 | +++ | IgG2a, K | | | | | | cells. CLL cells obtained from patients treated with ofatumumab were exposed to chimeric C8D3 mAb in vitro in the presence of human NK cells. The results are presented in FIG. 5.

These results show that chimeric C8D3 mAb mediated ADCC kills ofatumumab resistant CLL cells.

FIG. 6 shows that chimeric C8D3 mAb specifically binds tumor cells from patients with CLL, a CD20 expressing B-cell malignancy, who were treated with the anti-CD20 mAb ofatumumab. Anti-C3d mAb binding remains durable after the initial complement deposition.

Example 4

This example demonstrates binding of chimeric anti-C3d antibody C8D3 to immobilized C3d antigen. C3d antigen was immobilized and five different concentrations of anti-C3d Fab were analyzed by surface plasmon resonance on a Biacore 3000 instrument. Binding of the anti-C3d Fab to denatured antigen on polyvinylidene diflouride (PVDF) also was analyzed. The results are shown in FIG. 8. The anti-C3d Fab bound the antigen in both experiments, indicating the epitope is linear.

Example 5

The avidity of anti-C3d antibody C8D3 was compared to the avidity of an anti-CD20 antibody (Ofatumumab). The results are provided in FIG. 9, which shows that the anti-CD20 antibody exhibited a kD of 2.3 nM and the anti-C3d antibody exhibited a kD of 6.7 nM. This experiment indicates that after CLL cells have been subject to in vivo trogocytosis due to infusion of OFA in a CLL patient (OFA 24 h), they can no longer bind OFA. However, due to the deposition of complement fragments on the cells, at this time the C3d-opsonized cells can indeed bind the C3D8 mAb with high avidity, quite comparable to that observed for OFA on the "Pre" sample. These results confirm that CLL cells that lose CD20 upon OFA treatment can be successfully retargeted with an anti-C3d chimeric antibody as disclosed herein.

Example 6

The epitopes on C3d were mapped using PEPperCHIP technology (PEPperPRINT GmbH, Heidelberg, Germany). In brief, 15 amino acid (aa) long peptides with 14 aa overlaps were synthesized based on the C3d aa sequence and immobilized in duplicate on microarray chips. The peptide microarrays with the antigen-derived peptides were incubated with the anti-C3d murine antibodies from Example 1 (clones B7, C2, and C6) or the anti-C3d mouse-human chimeric antibody C8D3, and then stained with a secondary goat anti-human IgG (H+L) antibody conjugated to DyLight680. The microarrays were read using the LI-COR Odyssey Imaging System and then analyzed using PepSlide® Analyzer software. The results are presented in FIG. 10. The antibodies mapped to three epitopes (SEQ ID NOs: 16, 17, and 18), with C8D3 binding the third epitope of SEQ ID NO: 16.

To confirm the C8D3 epitope, an epitope 3 derived peptide (QYQKDAPDHQELNLDVSLQLPSR (SEQ ID NO: 19))

and a scrambled sequence peptide (LQPQNDVRDHSPYELQSLADLKQ (SEQ ID NO: 20)) were tested for ability to abrogate C8D3 binding to C3d antigen. The results are presented in FIG. 11, which shows that the epitope 3 peptide effectively abrogated binding, whereas the scrambled peptide had little or no effect, confirming the C8D3 epitope.

Example 7

The anti-tumor activity of anti-C3d chimeric antibody C8D3 was assessed in NOD/scid/IL-2R$\gamma^{null}$ (NSG) mice xenografted with Peripheral Blood Mononuclear Cells from Chronic Lymphocytic Leukemia (CLL) patients who had undergone treatment with Ofatumumab. After leukemic cell engraftment on day 1, mice were treated with 10 mg/kg isotype control or anti-C3d chimeric antibody C8D3 on days 5 and 7. Leukemic cell counts were quantified before treatment (day 5), after a single dose (day 7), and after a second dose (day 12). The results are shown in FIG. 12. Disease burden in the peripheral blood and spleens of the mice was quantified as previously described (Vire, Skarzynski et al. *Cancer Research*, Oct. 24, 2014; doi: 10.1158/0008-5472.CAN-14-2030). The results, presented in FIG. 13, demonstrate that the anti-C3d chimeric antibody is effective against CLL cells circulating in the peripheral blood (P=0.006) and residing in the spleens (P>0.0001) of xenografted mice. This is significant because NSG mouse spleens have been shown to support the activation and proliferation of CLL cells and, thus, resemble the lymph node microenvironment of CLL patients (Herman et al., *Blood*, 27.12:2311-2321, 2013).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and

The invention claimed is:

1. A method of killing a cancer cell having C3d complement protein on the surface thereof in a subject, the method comprising administering to the subject (1) an anti-C3d antibody or antibody fragment comprising a heavy chain variable region comprising
SEQ ID NO: 1 as heavy chain complementary determining region-1 (CDRH1);
SEQ ID NO: 2 as heavy chain complementary determining region-2 (CDRH2); and
SEQ ID NO: 3 or 4 as heavy chain complementary determining region-3 (CDRH3); and
a light chain variable region comprising
SEQ ID NO: 5 as light chain complementary determining region-1 (CDRL1);
SEQ ID NO: 6 as light chain complementary determining region-2 (CDRL2); and
SEQ ID NO: 7 as light chain complementary determining region-3 (CDRL3), and
(2) an antibody or antibody fragment to a cell surface protein other than C3d, wherein the antibody or antibody fragment to a cell surface protein other than C3d is an anti-CD33 antibody or antibody fragment, an anti-CD38 antibody or antibody fragment, an anti-EGFR antibody or antibody fragment, or an anti-ERBB2 antibody or antibody fragment,
and wherein administration of the antibody or antibody fragment to a cell surface protein other than C3d induces formation of C3d complement protein the surface of the cancer cell.

2. The method of claim 1, wherein the heavy chain variable region of the anti-C3d antibody or antibody fragment comprises SEQ ID NO: 3 as heavy chain complementary determining region-3 (CDRH3).

3. The method of claim 1, wherein the heavy chain variable region of the anti-C3d antibody or antibody fragment comprises SEQ ID NO: 4 as heavy chain complementary determining region-3 (CDRH3).

4. The method of claim 1, wherein the anti-C3d antibody or antibody fragment comprises a heavy chain comprising SEQ ID NO: 8 and a light chain comprising SEQ ID NO: 9.

5. The method of claim 1, wherein the anti-C3d antibody or antibody fragment comprises a heavy chain comprising SEQ ID NO: 10 and a light chain comprising SEQ ID NO: 11.

6. The method of claim 1, wherein the anti-C3d antibody or antibody fragment is selected from the group consisting of IgA1, IgA2, IgD, IgE, IgG1, IgG2, IgG3, IgG4, IgM, scFv, IgGΔCH$_2$, F(ab')2, scFv2CH3, F(ab), scFv4, scFv3, scFv2, dsFv, Fv, scFv-Fc, (scFv)2, a diabody, a T-body, a multispecific antibody, and a multivalent antibody.

7. The method of claim 1, wherein the anti-C3d antibody or antibody fragment is administered simultaneously with the administration of the antibody or antibody fragment to a cell surface protein other than C3d.

8. The method of claim 1, wherein the anti-C3d antibody or antibody fragment is administered sequentially in any order with the administration of the antibody or antibody fragment to a cell surface protein other than C3d.

9. The method of claim 1, wherein the antibody or antibody fragment to a cell surface protein other than C3d is an anti-CD33 antibody or antibody fragment.

10. The method of claim 9, wherein the cancer cell is a myeloid cell.

11. The method of claim 9, wherein the anti-CD33 antibody or antibody fragment is gemtuzumab or lintuzumab.

12. The method of claim 1, wherein the antibody or antibody fragment to a cell surface protein other than C3d is an anti-CD38 antibody or antibody fragment.

13. The method of claim 12, wherein the cancer cell is a plasma cell.

14. The method of claim 12, wherein the anti-CD38 antibody or antibody fragment is daratumumab.

15. The method of claim 1, wherein the antibody or antibody fragment to a cell surface protein other than C3d is an anti-EGFR antibody or antibody fragment.

16. The method of claim 15, wherein the cancer cell is from gut, colon, lung, breast, head, neck, pancreas, ovary, endometrium, or brain tissue.

17. The method of claim 15, wherein the anti-EGFR antibody or antibody fragment is cetuximab or panitumumab.

18. The method of claim 1, wherein the antibody or antibody fragment to a cell surface protein other than C3d is an anti-ERBB2 antibody or antibody fragment.

19. The method of claim 18, wherein the cancer cell is from gut, colon, lung, breast, head, neck, pancreas, ovary, endometrium, or brain tissue.

20. The method of claim 18, wherein the anti-ERBB2 antibody or antibody fragment is trastuzumab.

* * * * *